(12) United States Patent
Berez et al.

(10) Patent No.: US 9,855,047 B2
(45) Date of Patent: *Jan. 2, 2018

(54) FLEXIBLE VASCULAR OCCLUDING DEVICE

(71) Applicant: Covidien LP, Mansfied, MA (US)

(72) Inventors: Aaron Berez, Portola Valley, CA (US); Quang Tran, Atherton, CA (US)

(73) Assignee: Covidien LP, Mansfield, MA (US)

(*) Notice: Subject to any disclaimer, the term of this patent is extended or adjusted under 35 U.S.C. 154(b) by 172 days.

This patent is subject to a terminal disclaimer.

(21) Appl. No.: 14/791,876

(22) Filed: Jul. 6, 2015

(65) Prior Publication Data

US 2015/0305748 A1 Oct. 29, 2015

Related U.S. Application Data

(63) Continuation of application No. 13/845,162, filed on Mar. 18, 2013, now Pat. No. 9,125,659, which is a (Continued)

(51) Int. Cl.
*A61B 17/12* (2006.01)
*A61F 2/90* (2013.01)
(Continued)

(52) U.S. Cl.
CPC .. *A61B 17/12022* (2013.01); *A61B 17/12109* (2013.01); *A61B 17/12113* (2013.01);
(Continued)

(58) Field of Classification Search
CPC ........ A61B 17/12113; A61B 17/12118; A61B 2002/823; A61B 17/12022
(Continued)

(56) References Cited

U.S. PATENT DOCUMENTS 2,919,467 A 1/1960 Mercer
4,321,711 A 3/1982 Mano
(Continued)

FOREIGN PATENT DOCUMENTS

CN 101472537 A 7/2009
EP 855170 A2 7/1998
(Continued)

OTHER PUBLICATIONS

Benndorf, et al. Treatment of a Ruptured Dissecting Vertebral Artery Aneurysm with Double Stent Placement: Case Report AJNR Am J Neuroradiol, Nov.-Dec. 2001, vol. 22, pp. 1844-1848.
(Continued)

*Primary Examiner* — Thomas McEvoy
(74) *Attorney, Agent, or Firm* — Fortem IP LLP; Mary Fox

(57) ABSTRACT

A vascular occluding device for modifying blood flow in a vessel, while maintaining blood flow to the surrounding tissue. The occluding device includes a flexible, easily compressible and bendable occluding device that is particularly suited for treating aneurysms in the brain. The neurovascular occluding device can be deployed using a microcatheter. The occluding device can be formed by braiding wires in a helical fashion and can have varying lattice densities along the length of the occluding device. The occluding device could also have different lattice densities for surfaces on the same radial plane.

20 Claims, 15 Drawing Sheets

Related U.S. Application Data continuation of application No. 11/136,395, filed on May 25, 2005, now Pat. No. 8,398,701.

(60) Provisional application No. 60/574,429, filed on May 25, 2004.

(51) Int. Cl.
*A61B 17/00* (2006.01)
*A61F 2/82* (2013.01)

(52) U.S. Cl.
CPC .......... *A61B 17/12118* (2013.01); *A61F 2/90* (2013.01); *A61B 2017/00867* (2013.01); *A61B 2017/1205* (2013.01); *A61F 2002/823* (2013.01); *A61F 2230/001* (2013.01); *A61F 2230/0078* (2013.01); *A61F 2230/0091* (2013.01); *A61F 2230/0095* (2013.01)

(58) Field of Classification Search
USPC ....... 606/1.11, 1.12, 1.15–1.2, 1.4, 1.5, 1.51, 606/1.53
See application file for complete search history.

(56) References Cited

U.S. PATENT DOCUMENTS

| | | |
|---|---|---|
| 4,503,569 A | 3/1985 | Dotter |
| 4,512,338 A | 4/1985 | Balko et al. |
| 4,538,622 A | 9/1985 | Samson et al. |
| 4,572,186 A | 2/1986 | Gould et al. |
| 4,580,568 A | 4/1986 | Gianturco |
| 4,655,771 A | 4/1987 | Wallsten |
| 4,681,110 A | 7/1987 | Wiktor |
| 4,733,665 A | 3/1988 | Palmaz |
| 4,743,251 A | 5/1988 | Barra |
| 4,768,507 A | 9/1988 | Fischell et al. |
| 4,776,337 A | 10/1988 | Palmaz |
| 4,856,516 A | 8/1989 | Hillstead |
| 4,954,126 A | 9/1990 | Wallsten |
| 5,011,488 A | 4/1991 | Ginsburg |
| 5,035,706 A | 7/1991 | Giantureo et al. |
| 5,041,126 A | 8/1991 | Gianturco |
| 5,061,275 A | 10/1991 | Wallsten et al. |
| 5,108,416 A | 4/1992 | Ryan et al. |
| 5,160,341 A | 11/1992 | Brenneman et al. |
| 5,180,368 A | 1/1993 | Garrison |
| 5,192,297 A | 3/1993 | Hull |
| 5,197,978 A | 3/1993 | Hess |
| 5,201,757 A | 4/1993 | Heyn et al. |
| 5,209,731 A | 5/1993 | Sterman et al. |
| 5,242,399 A | 9/1993 | Lau et al. |
| 5,246,420 A | 9/1993 | Kraus et al. |
| 5,246,445 A | 9/1993 | Yachia et al. |
| 5,330,500 A | 7/1994 | Song |
| 5,336,205 A | 8/1994 | Zenzen et al. |
| 5,344,426 A | 9/1994 | Lau et al. |
| 5,360,443 A | 11/1994 | Barone et al. |
| 5,382,259 A | 1/1995 | Phelps et al. |
| 5,401,257 A | 3/1995 | Chevalier, Jr. et al. |
| 5,405,377 A | 4/1995 | Cragg |
| 5,405,380 A | 4/1995 | Gianotti et al. |
| 5,415,637 A | 5/1995 | Khosravi |
| 5,421,826 A | 6/1995 | Crocker et al. |
| 5,423,849 A | 6/1995 | Engelson et al. |
| 5,449,372 A | 9/1995 | Schmaltz et al. |
| 5,458,615 A | 10/1995 | Klemm et al. |
| 5,476,505 A | 12/1995 | Limon |
| 5,480,423 A | 1/1996 | Ravenscroft et al. |
| 5,484,444 A | 1/1996 | Braunschweiler |
| 5,489,295 A | 2/1996 | Piplani et al. |
| 5,507,767 A | 4/1996 | Maeda et al. |
| 5,507,768 A | 4/1996 | Lau et al. |
| 5,522,822 A | 6/1996 | Phelps et al. |
| 5,534,007 A | 7/1996 | St. Germain et al. |
| 5,545,208 A | 8/1996 | Wolff et al. |
| 5,546,880 A | 8/1996 | Ronyak et al. |
| 5,549,662 A | 8/1996 | Fordenbacher |
| 5,562,641 A | 10/1996 | Flomenblit et al. |
| 5,562,728 A | 10/1996 | Lazarus et al. |
| 5,591,225 A | 1/1997 | Okuda |
| 5,599,291 A | 2/1997 | Balbierz et al. |
| 5,601,593 A | 2/1997 | Freitag |
| 5,607,466 A | 3/1997 | Imbert et al. |
| 5,609,625 A | 3/1997 | Piplani et al. |
| 5,626,602 A | 5/1997 | Gianotti et al. |
| 5,628,783 A | 5/1997 | Quiachon et al. |
| 5,628,788 A | 5/1997 | Pinchuk |
| 5,632,771 A | 5/1997 | Boatman et al. |
| 5,632,772 A | 5/1997 | Alcime et al. |
| 5,636,641 A | 6/1997 | Fariabi |
| 5,637,113 A | 6/1997 | Tartaglia et al. |
| 5,639,278 A | 6/1997 | Dereume et al. |
| 5,645,559 A | 7/1997 | Hachtman et al. |
| D381,932 S | 8/1997 | Walshe et al. |
| 5,667,522 A | 9/1997 | Flomenblit et al. |
| 5,674,276 A | 10/1997 | Andersen et al. |
| 5,683,451 A | 11/1997 | Lenker et al. |
| 5,690,120 A | 11/1997 | Jacobsen |
| 5,690,644 A | 11/1997 | Yurek et al. |
| 5,695,499 A | 12/1997 | Helgerson et al. |
| 5,700,269 A | 12/1997 | Pinchuk et al. |
| 5,702,418 A | 12/1997 | Ravenscroft |
| 5,709,702 A | 1/1998 | Cogita |
| 5,709,703 A | 1/1998 | Lukic et al. |
| 5,718,159 A | 2/1998 | Thompson |
| 5,725,570 A | 3/1998 | Heath |
| 5,733,327 A | 3/1998 | Igaki et al. |
| 5,735,859 A | 4/1998 | Fischell et al. |
| 5,741,325 A | 4/1998 | Chaikof et al. |
| 5,741,333 A | 4/1998 | Frid |
| 5,746,765 A | 5/1998 | Kleshinski et al. |
| 5,749,883 A | 5/1998 | Halpern |
| 5,749,920 A | 5/1998 | Quiachon et al. |
| 5,769,884 A | 6/1998 | Solovay |
| 5,769,885 A | 6/1998 | Quiachon et al. |
| 5,776,099 A | 7/1998 | Tremulis |
| 5,776,142 A | 7/1998 | Gunderson |
| 5,782,909 A | 7/1998 | Quiachon et al. |
| 5,797,952 A | 8/1998 | Klein |
| 5,800,518 A | 9/1998 | Piplani et al. |
| 5,810,837 A | 9/1998 | Hofmann et al. |
| 5,817,102 A | 10/1998 | Johnson et al. |
| 5,817,105 A | 10/1998 | Van Der Brug |
| 5,824,039 A | 10/1998 | Piplani et al. |
| 5,824,041 A | 10/1998 | Lenker et al. |
| 5,824,042 A | 10/1998 | Lombardi et al. |
| 5,824,044 A | 10/1998 | Quiachon et al. |
| 5,824,058 A | 10/1998 | Ravenscroft et al. |
| 5,830,229 A | 11/1998 | Konya et al. |
| 5,833,632 A | 11/1998 | Jacobsen et al. |
| 5,836,868 A | 11/1998 | Ressemann et al. |
| 5,843,168 A | 12/1998 | Dang |
| 5,868,754 A | 2/1999 | Levine et al. |
| 5,876,419 A | 3/1999 | Carpenter et al. |
| 5,876,445 A | 3/1999 | Andersen |
| 5,888,201 A | 3/1999 | Stinson et al. |
| 5,902,266 A | 5/1999 | Leone et al. |
| 5,902,317 A | 5/1999 | Kleshinski et al. |
| 5,906,640 A | 5/1999 | Penn et al. |
| 5,911,717 A | 6/1999 | Jacobsen et al. |
| 5,916,194 A | 6/1999 | Jacobsen et al. |
| 5,919,204 A | 7/1999 | Lukic et al. |
| 5,928,260 A | 7/1999 | Chin et al. |
| 5,944,728 A | 8/1999 | Bates |
| 5,951,599 A | 9/1999 | McCrory |
| 5,957,973 A | 9/1999 | Quiachon et al. |
| 5,957,974 A | 9/1999 | Thompson et al. |
| 5,964,797 A | 10/1999 | Ho |
| 5,980,530 A | 11/1999 | Willard |
| 5,980,533 A | 11/1999 | Holman |
| 5,984,957 A | 11/1999 | Laptewicz, Jr. et al. |
| 6,012,277 A | 1/2000 | Prins et al. |
| 6,014,919 A | 1/2000 | Jacobsen et al. |

(56) References Cited

U.S. PATENT DOCUMENTS

| | | |
|---|---|---|
| 6,015,432 A | 1/2000 | Rakos et al. |
| 6,017,319 A | 1/2000 | Jacobsen et al. |
| 6,019,778 A | 2/2000 | Wilson et al. |
| 6,019,786 A | 2/2000 | Thompson |
| 6,022,369 A | 2/2000 | Jacobsen et al. |
| 6,024,754 A | 2/2000 | Engelson |
| 6,024,763 A | 2/2000 | Lenker et al. |
| 6,027,516 A | 2/2000 | Kolobow et al. |
| 6,033,436 A | 3/2000 | Steinke et al. |
| 6,039,721 A | 3/2000 | Johnson |
| 6,039,758 A | 3/2000 | Quiachon et al. |
| 6,042,589 A | 3/2000 | Marianne |
| 6,051,021 A | 4/2000 | Frid |
| 6,056,993 A | 5/2000 | Leidner et al. |
| 6,063,111 A | 5/2000 | Hieshima et al. |
| 6,074,407 A | 6/2000 | Levine et al. |
| 6,077,295 A | 6/2000 | Limon et al. |
| 6,080,191 A | 6/2000 | Summers |
| 6,083,257 A | 7/2000 | Taylor et al. |
| 6,093,199 A | 7/2000 | Brown et al. |
| 6,096,052 A | 8/2000 | Callister et al. |
| 6,102,942 A | 8/2000 | Ahari |
| 6,123,712 A | 9/2000 | Di Caprio et al. |
| 6,126,685 A | 10/2000 | Lenker et al. |
| 6,132,459 A | 10/2000 | Piplani et al. |
| 6,139,543 A | 10/2000 | Esch et al. |
| 6,146,415 A | 11/2000 | Fitz |
| 6,149,680 A | 11/2000 | Shelso et al. |
| 6,159,228 A | 12/2000 | Frid et al. |
| 6,161,399 A | 12/2000 | Jayaraman |
| 6,165,194 A | 12/2000 | Denardo |
| 6,165,210 A | 12/2000 | Lau et al. |
| 6,165,213 A | 12/2000 | Goicoechea et al. |
| 6,168,592 B1 | 1/2001 | Kupiecki et al. |
| 6,174,330 B1 | 1/2001 | Stinson |
| 6,183,410 B1 | 2/2001 | Jacobsen et al. |
| 6,183,508 B1 | 2/2001 | Stinson et al. |
| 6,187,013 B1 | 2/2001 | Stoltze et al. |
| 6,193,708 B1 | 2/2001 | Ken et al. |
| 6,197,046 B1 | 3/2001 | Piplani et al. |
| 6,203,569 B1 | 3/2001 | Wijay |
| 6,206,868 B1 | 3/2001 | Parodi |
| 6,210,400 B1 | 4/2001 | Hebert et al. |
| 6,210,434 B1 | 4/2001 | Quiachon et al. |
| 6,210,435 B1 | 4/2001 | Piplani et al. |
| 6,214,038 B1 | 4/2001 | Piplani et al. |
| 6,214,042 B1 | 4/2001 | Jacobsen et al. |
| 6,221,102 B1 | 4/2001 | Baker et al. |
| 6,224,609 B1 | 5/2001 | Ressemann et al. |
| 6,224,829 B1 | 5/2001 | Piplani et al. |
| 6,231,598 B1 | 5/2001 | Berry et al. |
| 6,235,050 B1 | 5/2001 | Quiachon et al. |
| 6,241,759 B1 | 6/2001 | Piplani et al. |
| 6,245,087 B1 | 6/2001 | Addis |
| 6,245,103 B1 | 6/2001 | Stinson |
| 6,251,132 B1 | 6/2001 | Ravenscroft et al. |
| 6,258,115 B1 | 7/2001 | Dubrul |
| 6,260,458 B1 | 7/2001 | Jacobsen et al. |
| 6,261,305 B1 | 7/2001 | Marotta et al. |
| 6,261,316 B1 | 7/2001 | Shaolian et al. |
| 6,264,671 B1 | 7/2001 | Stack et al. |
| 6,264,689 B1 | 7/2001 | Colgan et al. |
| 6,270,523 B1 | 8/2001 | Herweck et al. |
| 6,280,465 B1 | 8/2001 | Cryer |
| 6,283,991 B1 | 9/2001 | Cox et al. |
| 6,287,331 B1 | 9/2001 | Heath |
| 6,287,333 B1 | 9/2001 | Appling et al. |
| 6,290,721 B1 | 9/2001 | Heath |
| 6,299,636 B1 | 10/2001 | Schmitt et al. |
| 6,302,810 B2 | 10/2001 | Yokota |
| 6,302,893 B1 | 10/2001 | Limon et al. |
| 6,309,353 B1 | 10/2001 | Cheng et al. |
| 6,322,576 B1 | 11/2001 | Wallace et al. |
| 6,322,586 B1 | 11/2001 | Monroe et al. |
| 6,322,587 B1 | 11/2001 | Quiachon et al. |
| 6,325,826 B1 | 12/2001 | Vardi et al. |
| 6,334,871 B1 | 1/2002 | Dor et al. |
| 6,336,938 B1 | 1/2002 | Kavteladze et al. |
| 6,340,367 B1 | 1/2002 | Stinson et al. |
| 6,340,368 B1 | 1/2002 | Verbeck |
| 6,342,068 B1 | 1/2002 | Thompson |
| 6,344,041 B1 | 2/2002 | Kupiecki et al. |
| 6,348,063 B1 | 2/2002 | Yassour et al. |
| 6,350,199 B1 | 2/2002 | Williams et al. |
| 6,350,278 B1 | 2/2002 | Lenker et al. |
| 6,355,051 B1 | 3/2002 | Sisskind et al. |
| 6,355,061 B1 | 3/2002 | Quiachon |
| 6,364,895 B1 | 4/2002 | Greenhalgh |
| 6,368,339 B1 | 4/2002 | Amplatz |
| 6,368,344 B1 | 4/2002 | Fitz |
| 6,368,557 B1 | 4/2002 | Piplani et al. |
| 6,375,670 B1 | 4/2002 | Greenhalgh |
| 6,375,676 B1 | 4/2002 | Cox |
| 6,379,618 B1 | 4/2002 | Piplani et al. |
| 6,380,457 B1 | 4/2002 | Yurek et al. |
| 6,389,946 B1 | 5/2002 | Frid |
| 6,395,017 B1 | 5/2002 | Dwyer et al. |
| 6,395,021 B1 | 5/2002 | Hart et al. |
| 6,395,022 B1 | 5/2002 | Piplani et al. |
| 6,398,802 B1 | 6/2002 | Yee |
| 6,409,683 B1 | 6/2002 | Fonseca et al. |
| 6,413,235 B1 | 7/2002 | Parodi |
| 6,416,519 B1 | 7/2002 | VanDusseldorp |
| 6,416,536 B1 | 7/2002 | Yee |
| 6,419,693 B1 | 7/2002 | Fariabi |
| 6,428,489 B1 | 8/2002 | Jacobsen et al. |
| 6,440,088 B1 | 8/2002 | Jacobsen et al. |
| 6,443,971 B1 | 9/2002 | Boylan et al. |
| 6,443,979 B1 | 9/2002 | Stalker |
| 6,454,999 B1 | 9/2002 | Farhangnia et al. |
| 6,468,301 B1 | 10/2002 | Amplatz et al. |
| 6,477,768 B1 | 11/2002 | Wildner |
| 6,478,778 B1 | 11/2002 | Jacobsen et al. |
| 6,482,221 B1 | 11/2002 | Hebert et al. |
| 6,488,705 B2 | 12/2002 | Schmitt et al. |
| 6,491,648 B1 | 12/2002 | Cornish et al. |
| 6,494,895 B2 | 12/2002 | Addis |
| 6,497,711 B1 | 12/2002 | Plaia et al. |
| 6,503,450 B1 | 1/2003 | Afzal |
| 6,514,261 B1 | 2/2003 | Randall et al. |
| 6,514,285 B1 | 2/2003 | Pinchasik |
| 6,524,299 B1 | 2/2003 | Tran et al. |
| 6,527,763 B2 | 3/2003 | Esch et al. |
| 6,533,811 B1 | 3/2003 | Ryan et al. |
| 6,540,778 B1 | 4/2003 | Quiachon et al. |
| 6,547,779 B2 | 4/2003 | Levine |
| 6,551,352 B2 | 4/2003 | Clerc et al. |
| 6,572,646 B1 | 6/2003 | Boylan et al. |
| 6,576,006 B2 | 6/2003 | Limon et al. |
| 6,582,460 B1 | 6/2003 | Cryer |
| 6,582,461 B1 | 6/2003 | Burmeister et al. |
| 6,589,273 B1 | 7/2003 | McDermott |
| 6,592,616 B1 | 7/2003 | Stack et al. |
| 6,595,989 B1 | 7/2003 | Schaer |
| 6,602,271 B2 | 8/2003 | Adams et al. |
| 6,602,280 B2 | 8/2003 | Chobotov |
| 6,605,110 B2 | 8/2003 | Harrison |
| 6,613,075 B1 | 9/2003 | Healy et al. |
| 6,613,078 B1 | 9/2003 | Barone |
| 6,622,604 B1 | 9/2003 | Chouinard et al. |
| 6,623,518 B2 | 9/2003 | Thompson et al. |
| 6,635,068 B1 | 10/2003 | Dubrul et al. |
| 6,638,243 B2 | 10/2003 | Kupiecki |
| 6,645,240 B2 | 11/2003 | Yee |
| 6,646,218 B1 | 11/2003 | Campbell et al. |
| 6,652,508 B2 | 11/2003 | Griffin |
| 6,652,574 B1 | 11/2003 | Jayaraman |
| 6,656,212 B2 | 12/2003 | Ravenscroft et al. |
| 6,656,218 B1 | 12/2003 | Denardo et al. |
| 6,660,024 B1 | 12/2003 | Flaherty |
| 6,660,032 B2 | 12/2003 | Klumb et al. |
| 6,663,666 B1 | 12/2003 | Quiachon et al. |
| 6,666,881 B1 | 12/2003 | Richter et al. |
| 6,669,719 B2 | 12/2003 | Wallace |

(56) References Cited

U.S. PATENT DOCUMENTS

| | | |
|---|---|---|
| 6,673,089 B1 | 1/2004 | Yassour et al. |
| 6,673,100 B2 | 1/2004 | Diaz et al. |
| 6,679,893 B1 | 1/2004 | Tran |
| 6,682,557 B1 | 1/2004 | Quiachon et al. |
| 6,685,735 B1 | 2/2004 | Ahari |
| 6,689,120 B1 | 2/2004 | Gerdts |
| 6,689,162 B1 | 2/2004 | Thompson |
| 6,699,274 B2 | 3/2004 | Stinson |
| 6,702,843 B1 | 3/2004 | Brown et al. |
| 6,709,454 B1 | 3/2004 | Cox et al. |
| 6,712,834 B2 | 3/2004 | Yassour et al. |
| 6,726,700 B1 | 4/2004 | Levine |
| 6,733,519 B2 | 5/2004 | Lashinski et al. |
| 6,740,105 B2 | 5/2004 | Yodfat et al. |
| 6,740,112 B2 | 5/2004 | Yodfat et al. |
| 6,743,219 B1 | 6/2004 | Dwyer et al. |
| 6,755,855 B2 | 6/2004 | Yurek et al. |
| 6,758,885 B2 | 7/2004 | Leffel et al. |
| 6,767,361 B2 | 7/2004 | Quiachon et al. |
| 6,773,446 B1 | 8/2004 | Dwyer et al. |
| 6,793,667 B2 | 9/2004 | Hebert et al. |
| 6,814,746 B2 | 11/2004 | Thompson et al. |
| 6,814,748 B1 | 11/2004 | Baker et al. |
| 6,818,006 B2 | 11/2004 | Douk et al. |
| 6,833,003 B2 | 12/2004 | Jones et al. |
| 6,849,084 B2 | 2/2005 | Rabkin et al. |
| 6,858,034 B1 | 2/2005 | Hijlkema et al. |
| 6,860,893 B2 | 3/2005 | Wallace et al. |
| 6,860,898 B2 | 3/2005 | Stack et al. |
| 6,860,899 B1 | 3/2005 | Rivelli, Jr. |
| 6,860,900 B2 | 3/2005 | Clerc et al. |
| 6,860,901 B1 | 3/2005 | Baker et al. |
| 6,866,677 B2 | 3/2005 | Douk et al. |
| 6,866,679 B2 | 3/2005 | Kusleika |
| 6,866,680 B2 | 3/2005 | Yassour et al. |
| 6,881,221 B2 | 4/2005 | Golds |
| 6,887,267 B2 | 5/2005 | Dworschak et al. |
| 6,890,337 B2 | 5/2005 | Feeser et al. |
| 6,893,451 B2 | 5/2005 | Cano et al. |
| 6,918,921 B2 | 7/2005 | Brady et al. |
| 6,932,837 B2 | 8/2005 | Amplatz et al. |
| 6,936,055 B1 | 8/2005 | Ken et al. |
| 6,955,685 B2 | 10/2005 | Escamilla et al. |
| 6,960,227 B2 | 11/2005 | Jones et al. |
| 6,964,670 B1 | 11/2005 | Shah et al. |
| 6,964,672 B2 | 11/2005 | Brady et al. |
| 6,969,396 B2 | 11/2005 | Krolik et al. |
| 6,976,991 B2 | 12/2005 | Hebert et al. |
| 6,989,024 B2 | 1/2006 | Hebert et al. |
| 6,994,721 B2 | 2/2006 | Israel |
| 7,001,422 B2 | 2/2006 | Escamilla et al. |
| 7,004,962 B2 | 2/2006 | Stinson |
| 7,004,964 B2 | 2/2006 | Thompson et al. |
| 7,011,675 B2 | 3/2006 | Hemerick et al. |
| 7,037,330 B1 | 5/2006 | Rivelli, Jr. et al. |
| 7,041,129 B2 | 5/2006 | Rourke et al. |
| 7,066,951 B2 | 6/2006 | Chobotov |
| 7,069,835 B2 | 7/2006 | Nishri et al. |
| 7,074,236 B2 | 7/2006 | Rabkin et al. |
| 7,093,527 B2 | 8/2006 | Rapaport et al. |
| 7,101,392 B2 | 9/2006 | Heath |
| 7,107,105 B2 | 9/2006 | Bjorklund et al. |
| 7,118,539 B2 | 10/2006 | Vrba et al. |
| 7,118,594 B2 | 10/2006 | Quiachon et al. |
| 7,122,050 B2 | 10/2006 | Randall et al. |
| 7,137,990 B2 | 11/2006 | Hebert et al. |
| 7,166,125 B1 | 1/2007 | Baker et al. |
| 7,169,170 B2 | 1/2007 | Widenhouse |
| 7,169,172 B2 | 1/2007 | Levine et al. |
| 7,172,617 B2 | 2/2007 | Colgan et al. |
| 7,192,434 B2 | 3/2007 | Anderson et al. |
| 7,195,639 B2 | 3/2007 | Quiachon et al. |
| 7,195,648 B2 | 3/2007 | Jones et al. |
| 7,201,768 B2 | 4/2007 | Diaz et al. |
| 7,201,769 B2 | 4/2007 | Jones et al. |
| 7,211,109 B2 | 5/2007 | Thompson |
| 7,213,495 B2 | 5/2007 | McCullagh et al. |
| 7,220,271 B2 | 5/2007 | Clubb et al. |
| 7,235,096 B1 | 6/2007 | Van Tassel et al. |
| 7,264,632 B2 | 9/2007 | Wright et al. |
| 7,275,471 B2 | 10/2007 | Nishri et al. |
| 7,279,005 B2 | 10/2007 | Stinson |
| 7,279,208 B1 | 10/2007 | Goffena et al. |
| 7,294,137 B2 | 11/2007 | Rivelli, Jr. et al. |
| 7,294,146 B2 | 11/2007 | Chew et al. |
| 7,300,456 B2 | 11/2007 | Andreas et al. |
| 7,300,460 B2 | 11/2007 | Levine et al. |
| 7,306,624 B2 | 12/2007 | Yodfat et al. |
| 7,309,351 B2 | 12/2007 | Escamilla et al. |
| 7,311,031 B2 | 12/2007 | McCullagh et al. |
| 7,320,702 B2 | 1/2008 | Hammersmark et al. |
| 7,323,001 B2 | 1/2008 | Clubb et al. |
| 7,331,973 B2 | 2/2008 | Gesswein et al. |
| 7,331,976 B2 | 2/2008 | McGuckin, Jr. et al. |
| 7,331,985 B2 | 2/2008 | Thompson et al. |
| 7,338,518 B2 | 3/2008 | Chobotov |
| 7,438,712 B2 | 10/2008 | Chouinard |
| 7,462,192 B2 | 12/2008 | Norton et al. |
| 7,468,070 B2 | 12/2008 | Henry et al. |
| 7,470,282 B2 | 12/2008 | Shelso |
| 7,473,271 B2 | 1/2009 | Gunderson |
| 7,491,224 B2 | 2/2009 | Cox et al. |
| 7,520,893 B2 | 4/2009 | Rivelli, Jr. |
| RE40,816 E | 6/2009 | Taylor et al. |
| 7,572,288 B2 | 8/2009 | Cox |
| 7,572,290 B2 | 8/2009 | Yodfat et al. |
| 7,588,597 B2 | 9/2009 | Frid |
| 7,695,507 B2 | 4/2010 | Rivelli, Jr. et al. |
| 7,763,011 B2 | 7/2010 | Ortiz et al. |
| 7,771,463 B2 | 8/2010 | Ton et al. |
| 7,854,760 B2 | 12/2010 | Molaei et al. |
| 7,901,447 B2 | 3/2011 | Molaei et al. |
| 7,942,925 B2 | 5/2011 | Yodfat et al. |
| 8,007,529 B2 | 8/2011 | Yan |
| 8,092,486 B2 | 1/2012 | Berrada et al. |
| 8,092,508 B2 | 1/2012 | Leynov et al. |
| 8,192,484 B2 | 6/2012 | Frid |
| 8,382,825 B2 | 2/2013 | Garcia et al. |
| 8,394,119 B2 | 3/2013 | Zaver et al. |
| 8,398,701 B2 | 3/2013 | Berez et al. |
| 8,617,234 B2 | 12/2013 | Garcia et al. |
| 8,623,067 B2 | 1/2014 | Berez et al. |
| 8,628,564 B2 | 1/2014 | Berez et al. |
| 8,764,817 B2 | 7/2014 | Sheldon |
| 8,801,772 B2 | 8/2014 | Shobayashi et al. |
| 8,979,918 B2 | 3/2015 | Murayama |
| 9,050,205 B2 | 6/2015 | Berez et al. |
| 9,114,001 B2 | 8/2015 | Kusleika et al. |
| 9,125,659 B2 | 9/2015 | Berez et al. |
| 2001/0027338 A1 | 10/2001 | Greenberg |
| 2001/0044651 A1 | 11/2001 | Steinke et al. |
| 2001/0049547 A1 | 12/2001 | Moore |
| 2001/0056299 A1 | 12/2001 | Thompson |
| 2002/0004667 A1 | 1/2002 | Adams et al. |
| 2002/0007194 A1 | 1/2002 | Plowiecki |
| 2002/0029061 A1 | 3/2002 | Amplatz et al. |
| 2002/0035396 A1 | 3/2002 | Heath |
| 2002/0062091 A1 | 5/2002 | Jacobsen et al. |
| 2002/0078808 A1 | 6/2002 | Jacobsen et al. |
| 2002/0082558 A1 | 6/2002 | Samson et al. |
| 2002/0087119 A1 | 7/2002 | Parodi |
| 2002/0111633 A1 | 8/2002 | Stoltze et al. |
| 2002/0111648 A1 | 8/2002 | Kusleika et al. |
| 2002/0120323 A1 | 8/2002 | Thompson et al. |
| 2002/0138133 A1 | 9/2002 | Lenz et al. |
| 2002/0143361 A1 | 10/2002 | Douk et al. |
| 2002/0143384 A1 | 10/2002 | Ozasa |
| 2002/0169473 A1 | 11/2002 | Sepetka et al. |
| 2002/0169474 A1 | 11/2002 | Kusleika et al. |
| 2002/0173839 A1 | 11/2002 | Leopold et al. |
| 2002/0188314 A1 | 12/2002 | Anderson et al. |
| 2002/0193864 A1 | 12/2002 | Khosravi et al. |
| 2003/0009215 A1 | 1/2003 | Mayer |
| 2003/0023299 A1 | 1/2003 | Amplatz et al. |

(56) References Cited

U.S. PATENT DOCUMENTS

| | | |
|---|---|---|
| 2003/0069522 A1 | 4/2003 | Jacobsen et al. |
| 2003/0100945 A1 | 5/2003 | Yodfat et al. |
| 2003/0130684 A1 | 7/2003 | Brady et al. |
| 2003/0135258 A1 | 7/2003 | Andreas et al. |
| 2003/0163155 A1 | 8/2003 | Haverkost et al. |
| 2003/0163156 A1 | 8/2003 | Hebert et al. |
| 2003/0176884 A1 | 9/2003 | Berrada et al. |
| 2003/0187495 A1 | 10/2003 | Cully et al. |
| 2003/0212429 A1 | 11/2003 | Keegan et al. |
| 2003/0212430 A1 | 11/2003 | Bose et al. |
| 2004/0024416 A1 | 2/2004 | Yodfat et al. |
| 2004/0030265 A1 | 2/2004 | Murayama et al. |
| 2004/0044395 A1 | 3/2004 | Nelson |
| 2004/0073300 A1 | 4/2004 | Chouinard et al. |
| 2004/0088037 A1 | 5/2004 | Nachreiner et al. |
| 2004/0093010 A1 | 5/2004 | Gesswein et al. |
| 2004/0098099 A1 | 5/2004 | McCullagh et al. |
| 2004/0133223 A1 | 7/2004 | Weber |
| 2004/0153117 A1 | 8/2004 | Clubb et al. |
| 2004/0162606 A1 | 8/2004 | Thompson |
| 2004/0172055 A1 | 9/2004 | Huter et al. |
| 2004/0186368 A1 | 9/2004 | Ramzipoor et al. |
| 2004/0193178 A1 | 9/2004 | Nikolchev |
| 2004/0193179 A1 | 9/2004 | Nikolchev |
| 2004/0193208 A1 | 9/2004 | Talpade et al. |
| 2004/0199243 A1 | 10/2004 | Yodfat |
| 2004/0210235 A1 | 10/2004 | Deshmukh et al. |
| 2004/0215332 A1 | 10/2004 | Frid |
| 2004/0220585 A1 | 11/2004 | Nikolchev |
| 2004/0220608 A1 | 11/2004 | D'Aquanni et al. |
| 2004/0220663 A1 | 11/2004 | Rivelli |
| 2004/0254628 A1 | 12/2004 | Nazzaro et al. |
| 2004/0260331 A1 | 12/2004 | D'Aquanni et al. |
| 2005/0004595 A1 | 1/2005 | Boyle |
| 2005/0021075 A1 | 1/2005 | Bonnette et al. |
| 2005/0033407 A1 | 2/2005 | Weber et al. |
| 2005/0038447 A1 | 2/2005 | Huffmaster |
| 2005/0051243 A1 | 3/2005 | Forbes Jones et al. |
| 2005/0055047 A1 | 3/2005 | Greenhalgh |
| 2005/0059889 A1 | 3/2005 | Mayer |
| 2005/0060017 A1 | 3/2005 | Fischell et al. |
| 2005/0090888 A1 | 4/2005 | Hines et al. |
| 2005/0101989 A1 | 5/2005 | Cully et al. |
| 2005/0137680 A1 | 6/2005 | Ortiz et al. |
| 2005/0149111 A1 | 7/2005 | Kanazawa et al. |
| 2005/0165441 A1 | 7/2005 | McGuckin et al. |
| 2005/0177186 A1 | 8/2005 | Cully et al. |
| 2005/0192620 A1 | 9/2005 | Cully et al. |
| 2005/0197689 A1 | 9/2005 | Molaei |
| 2005/0209672 A1 | 9/2005 | George et al. |
| 2005/0209678 A1 | 9/2005 | Henkes et al. |
| 2005/0246010 A1 | 11/2005 | Alexander et al. |
| 2005/0267568 A1 | 12/2005 | Berez et al. |
| 2005/0283220 A1 | 12/2005 | Gobran et al. |
| 2005/0288764 A1 | 12/2005 | Snow |
| 2005/0288766 A1 | 12/2005 | Plain et al. |
| 2006/0020324 A1 | 1/2006 | Schmid et al. |
| 2006/0036309 A1 | 2/2006 | Hebert et al. |
| 2006/0089703 A1 | 4/2006 | Escamilla et al. |
| 2006/0095213 A1 | 5/2006 | Escamilla et al. |
| 2006/0111771 A1 | 5/2006 | Ton et al. |
| 2006/0116713 A1 | 6/2006 | Sepetka et al. |
| 2006/0116750 A1 | 6/2006 | Hebert et al. |
| 2006/0184238 A1 | 8/2006 | Kaufmann et al. |
| 2006/0195118 A1 | 8/2006 | Richardson |
| 2006/0206148 A1 | 9/2006 | Khairkhahan et al. |
| 2006/0206200 A1 | 9/2006 | Garcia et al. |
| 2006/0206201 A1 | 9/2006 | Garcia et al. |
| 2006/0212127 A1 | 9/2006 | Karabey et al. |
| 2006/0271149 A1 | 11/2006 | Berez et al. |
| 2006/0271153 A1 | 11/2006 | Garcia et al. |
| 2006/0276910 A1 | 12/2006 | Weber |
| 2007/0021816 A1 | 1/2007 | Rudin |
| 2007/0043419 A1 | 2/2007 | Nikolchev et al. |
| 2007/0055365 A1 | 3/2007 | Greenberg et al. |
| 2007/0060994 A1 | 3/2007 | Gobran et al. |
| 2007/0073379 A1 | 3/2007 | Chang |
| 2007/0077347 A1 | 4/2007 | Richter |
| 2007/0100321 A1 | 5/2007 | Rudakov et al. |
| 2007/0100414 A1 | 5/2007 | Licata |
| 2007/0100430 A1 | 5/2007 | Rudakov et al. |
| 2007/0112415 A1 | 5/2007 | Bartlett |
| 2007/0119295 A1 | 5/2007 | McCullagh |
| 2007/0123969 A1 | 5/2007 | Gianotti |
| 2007/0162104 A1 | 7/2007 | Frid |
| 2007/0167980 A1 | 7/2007 | Figulla et al. |
| 2007/0198076 A1 | 8/2007 | Hebert et al. |
| 2007/0203559 A1 | 8/2007 | Freudenthal et al. |
| 2007/0203563 A1 | 8/2007 | Hebert et al. |
| 2007/0208367 A1 | 9/2007 | Fiorella et al. |
| 2007/0208373 A1 | 9/2007 | Zaver et al. |
| 2007/0208376 A1 | 9/2007 | Meng |
| 2007/0208415 A1 | 9/2007 | Grotheim et al. |
| 2007/0219619 A1 | 9/2007 | Dieck et al. |
| 2007/0225760 A1 | 9/2007 | Moszner et al. |
| 2007/0233175 A1 | 10/2007 | Zaver et al. |
| 2007/0239261 A1 | 10/2007 | Bose et al. |
| 2007/0255386 A1 | 11/2007 | Tenne |
| 2007/0255388 A1 | 11/2007 | Rudakov et al. |
| 2007/0280850 A1 | 12/2007 | Carlson |
| 2007/0299500 A1 | 12/2007 | Hebert et al. |
| 2007/0299501 A1 | 12/2007 | Hebert et al. |
| 2007/0299502 A1 | 12/2007 | Hebert et al. |
| 2008/0015673 A1 | 1/2008 | Chuter |
| 2008/0033341 A1 | 2/2008 | Grad |
| 2008/0033526 A1 | 2/2008 | Atladottir et al. |
| 2008/0039930 A1 | 2/2008 | Jones et al. |
| 2008/0039933 A1 | 2/2008 | Yodfat |
| 2008/0071351 A1 | 3/2008 | Flanagan et al. |
| 2008/0082154 A1 | 4/2008 | Tseng et al. |
| 2008/0114391 A1 | 5/2008 | Dieck et al. |
| 2008/0119943 A1 | 5/2008 | Armstrong et al. |
| 2008/0125855 A1 | 5/2008 | Henkes et al. |
| 2008/0208320 A1 | 8/2008 | Tan-Malecki et al. |
| 2008/0221666 A1 | 9/2008 | Licata et al. |
| 2008/0221670 A1 | 9/2008 | Clerc et al. |
| 2008/0221671 A1 | 9/2008 | Chouinard et al. |
| 2008/0255654 A1 | 10/2008 | Hebert et al. |
| 2008/0255655 A1 | 10/2008 | Kusleika et al. |
| 2008/0262590 A1 | 10/2008 | Murray |
| 2008/0269774 A1 | 10/2008 | Garcia et al. |
| 2008/0275497 A1 | 11/2008 | Palmer et al. |
| 2008/0275498 A1 | 11/2008 | Palmer et al. |
| 2008/0294104 A1 | 11/2008 | Mawad |
| 2008/0300667 A1 | 12/2008 | Hebert et al. |
| 2008/0300668 A1 | 12/2008 | Bonsignore |
| 2008/0300673 A1 | 12/2008 | Clerc et al. |
| 2009/0024202 A1 | 1/2009 | Dave et al. |
| 2009/0024205 A1 | 1/2009 | Hebert et al. |
| 2009/0030496 A1 | 1/2009 | Kaufmann |
| 2009/0030497 A1 | 1/2009 | Metcalf et al. |
| 2009/0054981 A1 | 2/2009 | Frid et al. |
| 2009/0099643 A1 | 4/2009 | Hyodoh et al. |
| 2009/0105802 A1 | 4/2009 | Henry et al. |
| 2009/0105803 A1 | 4/2009 | Shelso |
| 2009/0125093 A1 | 5/2009 | Hansen |
| 2009/0192536 A1 | 7/2009 | Berez et al. |
| 2009/0192587 A1 | 7/2009 | Frid |
| 2009/0198318 A1 | 8/2009 | Berez et al. |
| 2009/0216307 A1 | 8/2009 | Kaufmann et al. |
| 2009/0222035 A1 | 9/2009 | Schneiderman |
| 2009/0270974 A1 | 10/2009 | Berez et al. |
| 2009/0287241 A1 | 11/2009 | Berez et al. |
| 2009/0287288 A1 | 11/2009 | Berez et al. |
| 2009/0288000 A1 | 11/2009 | McPherson |
| 2009/0292348 A1 | 11/2009 | Berez et al. |
| 2009/0318947 A1 | 12/2009 | Garcia et al. |
| 2009/0319017 A1 | 12/2009 | Berez et al. |
| 2010/0010624 A1 | 1/2010 | Berez et al. |
| 2010/0042200 A1 | 2/2010 | Richter et al. |
| 2010/0061604 A1 | 3/2010 | Nahm et al. |
| 2010/0063531 A1 | 3/2010 | Rudakov et al. |
| 2010/0070024 A1 | 3/2010 | Venturelli et al. |
| 2010/0076317 A1 | 3/2010 | Babic et al. |

(56) References Cited

U.S. PATENT DOCUMENTS

| | | | |
|---|---|---|---|
| 2010/0152834 A1 | 6/2010 | Hannes et al. |
| 2010/0161025 A1 | 6/2010 | Kuppurathanam et al. |
| 2010/0174269 A1 | 7/2010 | Tompkins et al. |
| 2010/0174309 A1 | 7/2010 | Fulkerson et al. |
| 2010/0179583 A1 | 7/2010 | Carpenter et al. |
| 2010/0179647 A1 | 7/2010 | Carpenter et al. |
| 2010/0198334 A1 | 8/2010 | Yodfat et al. |
| 2010/0204779 A1 | 8/2010 | Schuessler et al. |
| 2010/0211154 A1 | 8/2010 | Murayama |
| 2010/0222864 A1 | 9/2010 | Rivelli, Jr. et al. |
| 2010/0241214 A1 | 9/2010 | Holzer et al. |
| 2010/0256732 A1 | 10/2010 | Shin et al. |
| 2010/0256733 A1 | 10/2010 | Schuessler |
| 2010/0280587 A1 | 11/2010 | Ortiz et al. |
| 2010/0318174 A1 | 12/2010 | Shaolian et al. |
| 2010/0318178 A1 | 12/2010 | Rapaport et al. |
| 2011/0016427 A1 | 1/2011 | Douen |
| 2011/0040372 A1 | 2/2011 | Hansen et al. |
| 2011/0046718 A1 | 2/2011 | Cattaneo |
| 2011/0046720 A1 | 2/2011 | Shalev et al. |
| 2011/0054589 A1 | 3/2011 | Bashiri et al. |
| 2011/0166592 A1 | 7/2011 | Garcia et al. |
| 2011/0166637 A1 | 7/2011 | Irwin et al. |
| 2011/0166639 A1 | 7/2011 | Pulnev et al. |
| 2011/0179389 A1 | 7/2011 | Douen |
| 2011/0184451 A1 | 7/2011 | Sahl |
| 2011/0190862 A1 | 8/2011 | Bashiri et al. |
| 2011/0245862 A1 | 10/2011 | Dieck et al. |
| 2011/0270178 A1 | 11/2011 | Fiorella et al. |
| 2012/0035643 A1 | 2/2012 | Khairkhahan et al. |
| 2012/0041459 A1 | 2/2012 | Fiorella et al. |
| 2012/0158124 A1 | 6/2012 | Zaver et al. |
| 2012/0253454 A1 | 10/2012 | Costello |
| 2012/0290067 A1 | 11/2012 | Cam et al. |
| 2012/0316638 A1 | 12/2012 | Grad et al. |
| 2012/0323309 A1 | 12/2012 | Cattaneo |
| 2013/0116773 A1 | 5/2013 | Roeder et al. |
| 2013/0123901 A1 | 5/2013 | Connor et al. |
| 2013/0138202 A1 | 5/2013 | Paul et al. |
| 2013/0172975 A1 | 7/2013 | Berez et al. |
| 2013/0190856 A1 | 7/2013 | von Oepen et al. |
| 2013/0204347 A1 | 8/2013 | Armstrong et al. |
| 2013/0211489 A1 | 8/2013 | Makower et al. |
| 2013/0211497 A1 | 8/2013 | Charlebois et al. |
| 2013/0274849 A1 | 10/2013 | Zaver et al. |
| 2014/0018843 A1 | 1/2014 | Berez et al. |
| 2014/0074149 A1 | 3/2014 | Garcia et al. |
| 2014/0121744 A1 | 5/2014 | Kusleika |
| 2014/0121746 A1 | 5/2014 | Kusleika et al. |
| 2014/0128957 A1 | 5/2014 | Losordo et al. |
| 2014/0222130 A1 | 8/2014 | Kusleika |
| 2014/0316454 A1 | 10/2014 | Zaver et al. |
| 2014/0336741 A1 | 11/2014 | Connor et al. |

FOREIGN PATENT DOCUMENTS

| | | |
|---|---|---|
| EP | 1683541 A2 | 7/2006 |
| EP | 1942972 A1 | 7/2008 |
| EP | 1872742 B1 | 5/2009 |
| EP | 2 078 512 A1 | 7/2009 |
| EP | 1750619 | 7/2013 |
| FR | 2556210 B1 | 4/1988 |
| JP | 10-328216 A | 12/1998 |
| JP | 11-506686 | 6/1999 |
| JP | 11-299901 A | 11/1999 |
| JP | 2001-509412 A | 7/2001 |
| JP | 2002-253682 A | 9/2002 |
| JP | 2003-520103 A | 7/2003 |
| JP | 2004-049585 A | 2/2004 |
| JP | 2005-074230 A | 3/2005 |
| JP | 2006-506201 A | 2/2006 |
| JP | 2008-502378 A | 1/2008 |
| JP | 2008-541832 A | 11/2008 |
| WO | WO-88/00813 A1 | 2/1988 |
| WO | WO-95/009586 A1 | 4/1995 |
| WO | WO-95/032757 A1 | 12/1995 |
| WO | WO-98/004211 A1 | 2/1998 |
| WO | WO-98/47447 A1 | 10/1998 |
| WO | WO-99/002092 A1 | 1/1999 |
| WO | WO-99/05977 A1 | 2/1999 |
| WO | WO-99/049812 A3 | 12/1999 |
| WO | WO-01/005331 A1 | 1/2001 |
| WO | WO-01/052771 A1 | 7/2001 |
| WO | WO-02/005729 | 1/2002 |
| WO | WO-02/047579 | 6/2002 |
| WO | WO-02/054988 A3 | 1/2003 |
| WO | WO-03/007840 A2 | 1/2003 |
| WO | WO-03/043527 A2 | 5/2003 |
| WO | WO-03/049600 A2 | 6/2003 |
| WO | WO-03/057079 A1 | 7/2003 |
| WO | WO-03/073963 A2 | 9/2003 |
| WO | WO-2004/087006 A3 | 11/2004 |
| WO | WO-2005/021061 A2 | 3/2005 |
| WO | WO-2005/023149 A3 | 12/2005 |
| WO | WO-2006/034140 A2 | 3/2006 |
| WO | WO-2006/073745 A2 | 7/2006 |
| WO | WO-2006/127005 A1 | 11/2006 |
| WO | WO-2007/122396 A1 | 11/2007 |
| WO | WO-2008/005898 A2 | 1/2008 |
| WO | WO-2007/139689 A3 | 9/2008 |
| WO | WO-2007/139699 A3 | 9/2008 |
| WO | WO-2008/156683 A1 | 12/2008 |
| WO | WO-2005/115118 A3 | 7/2009 |
| WO | WO-2009/105710 A1 | 8/2009 |
| WO | WO-2010/127838 A2 | 11/2010 |
| WO | WO-2011/023105 A1 | 3/2011 |
| WO | WO-2011/134663 A2 | 11/2011 |

OTHER PUBLICATIONS

Brilstra, et al., Treatment of Intracranial Aneurysms by Embolization with Coils: A Systematic Review, Stroke, Journal of the American Heart Association, 1999, vol. 30, pp. 470-476.

Ferguson, Gary, Physical Factors in the Initiation, Growth and Rupture of Human Intracranial Saccular Aneurysms, J. Neurosurg, Dec. 1972, vol. 37, pp. 666-667.

Geremia, et al., Embolization of Experimentally Created Aneurysms with Intravascular Stent Devices, ANJR American Journal of Neuroradiology, Aug. 1994, vol. 15, pp. 1223-1231.

Geremia, et al., Occlusion of Experimentally Created Fusiform Aneurysms with Porous Metallic Stents, ANJR Am J Neuroradiol, Apr. 2000, Issue 21, pp. 739-745.

Lanzino, et al., Efficacy and Current Limitations of Intravascular Stents for Intracranial Internal Carotid, Vertebral, and Basilar Artery Aneurysms, Journal of Neurosurgery, Oct. 1999, vol. 91, Issue 4, pp. 538-546.

Lieber, et al., Alteration of Hemodynamics in Aneurysm Models by Stenting: Influence of Stent Porosity, Ann of Biomedical Eng., 1997, vol. 25, pp. 460-469, Buffalo, NY.

Lieber, et al., The Physics of Endoluminal Stenting in the Treatment of Cerebrovascular Aneurysms, Neurological Research, 2002, Vcol 24, Issue Supplement 1, pp. S32-S42.

Moss, et al., Vascular Occlusion with a Balloon-Expandable Stent Occluder, Radiology, May 1994, vol. 191, Issue 2, pp. 483-486.

Pereira, Edgard, History of Endovascular Aneurysm Occlusion, Management of Cerebral Aneurysms, 2004, pp. 11-26.

Qureshi, Adnan, Endovascular Treatment of Cerebrovascular Diseases and Intracranial Neoplasms, The Lancelet, Mar. 2004, vol. 363, pp. 804-813.

Steiger, Pathophysiology of Development and Rupture of Cerebral Aneurysms, Acta Nurochirurgica, Mar. 1990, Vol Supplementum 48, Pages in 62 pages.

Tenaglia, et al., Ultrasound Guide Wire-Directed Stent Deployment, Duke University Medical Center, Department of Medicine, 1993 USA.

Yu, et al., A Steady Flow Analysis on the Stented and Non-Stented Sidewall Aneurysm Models, Medical Engineering and Physics, Apr. 1999, Issue 21, pp. 133-141.

U.S. Appl. No. 14/714,619, filed May 18, 2015.
U.S. Appl. No. 14/833,768, filed Aug. 24, 2015.

(56) References Cited

OTHER PUBLICATIONS

Opposition to European Patent No. 2626038; date of opposition Jun. 14, 2017; 27 pages.
Gal, Gyula, New Devices for Exclusion of Cerebral Aneurysms, Excerpt from Urgent Interventional Therapies, first edition 2015, John Wiley & Sons Ltd., chapter 35, pp. 302-312.
Maldonado et al., Stent-Assisted Techniques for Intracranial Aneurysms, chapter 14, 2012, pp. 291-312.
Http://www.balt.fr/en/technologie, Balt Extrusion, A sustainable growth thanks to a mastered and controlled industrial design, 4 pages; date of access: Jun. 8, 2017.

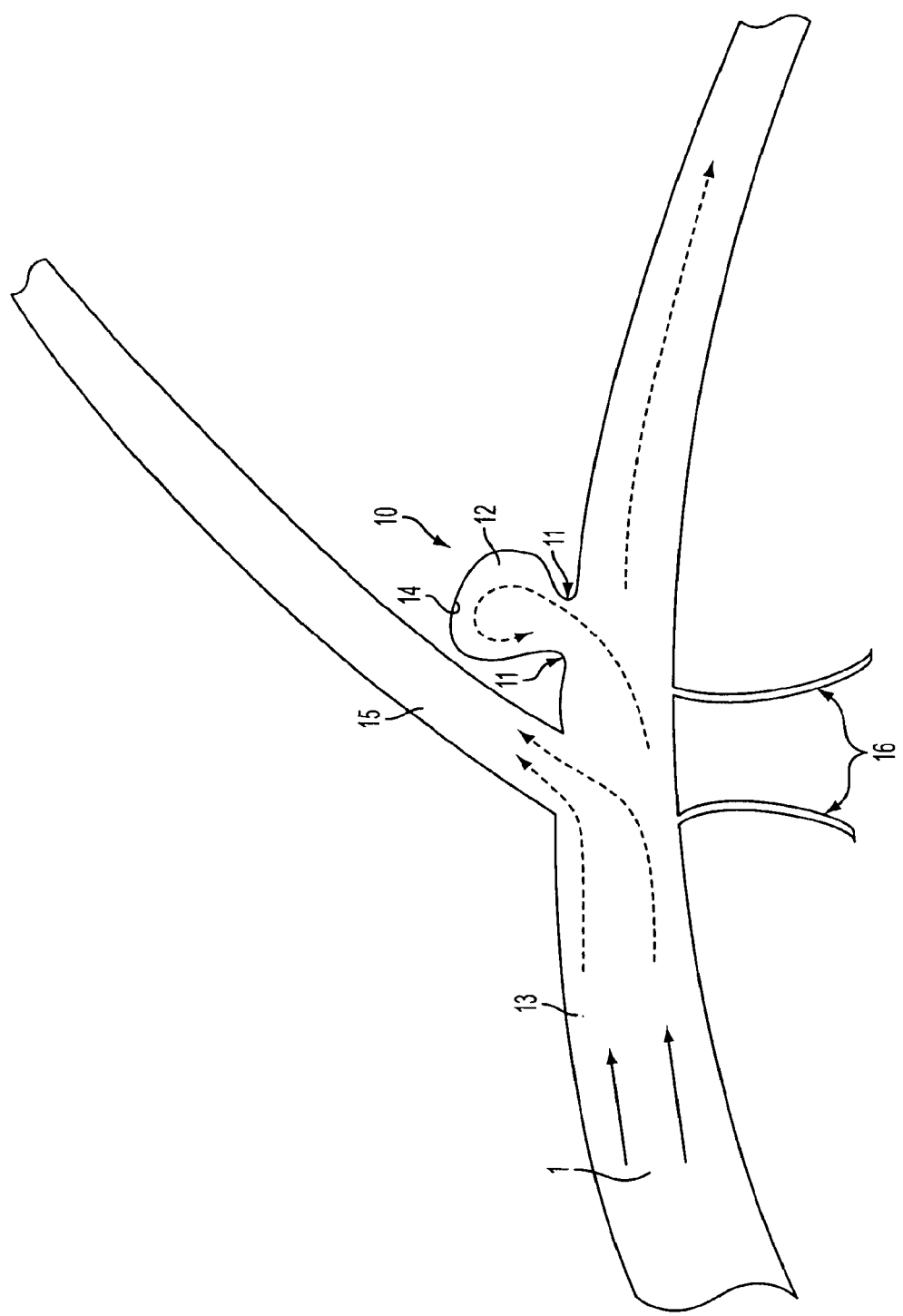

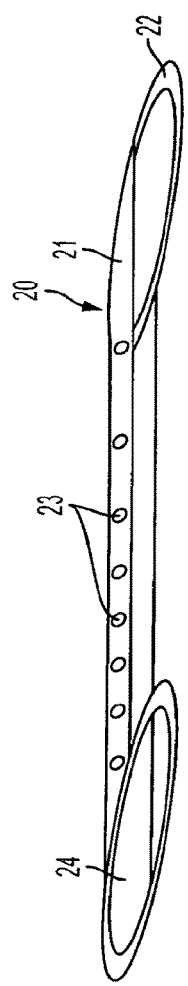
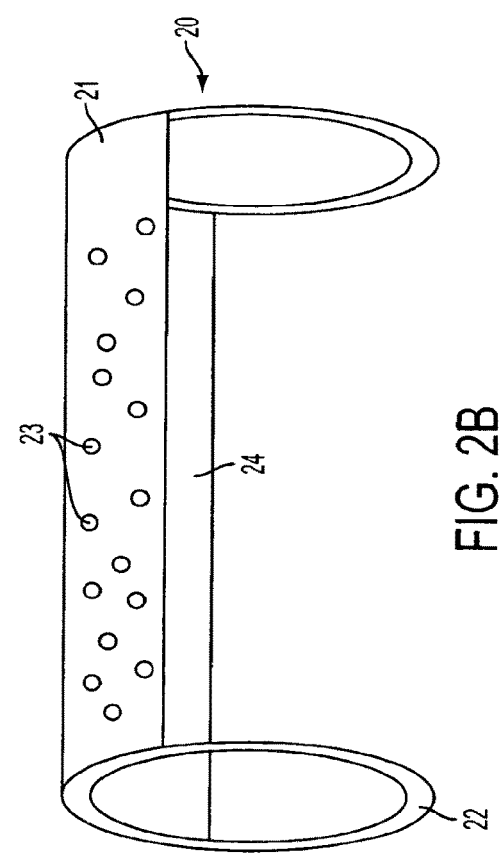
FIG. 2A
FIG. 2B

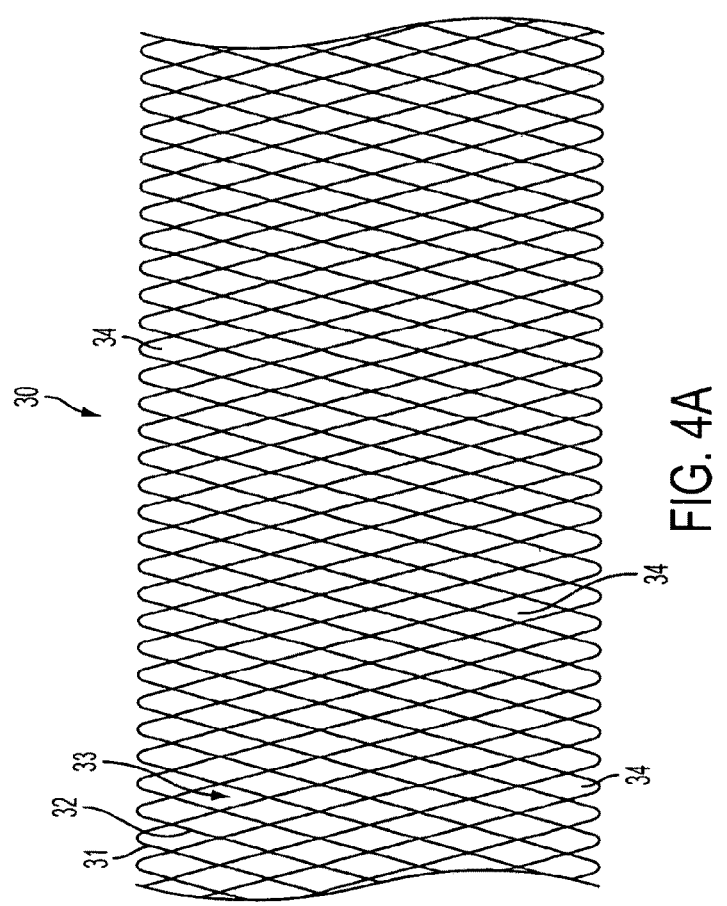
FIG. 4A
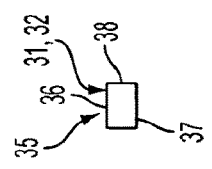
FIG. 4C
FIG. 4B

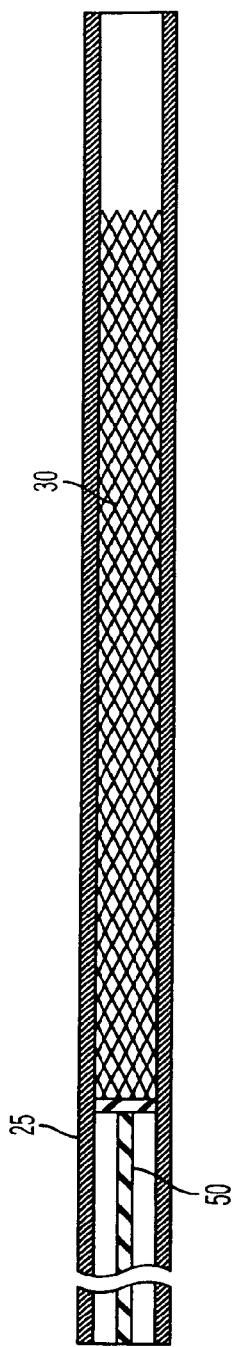
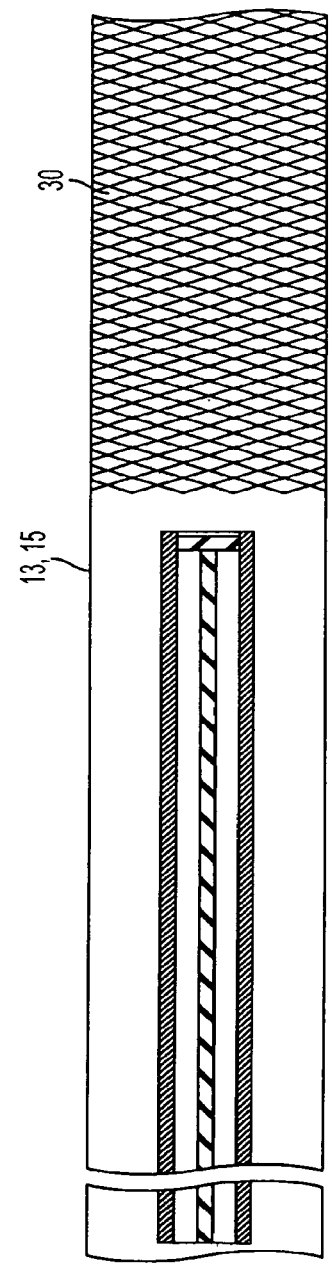
FIG. 5
FIG. 6

FLEXIBLE VASCULAR OCCLUDING DEVICE

RELATED APPLICATION

This application is a continuation of U.S. patent application Ser. No. 13/845,162, filed Mar. 18, 2013, which is a continuation of U.S. patent application Ser. No. 11/136,395, filed on May 25, 2005, now issued as U.S. Pat. No. 8,398,701, which claims priority benefit of U.S. Provisional Application Ser. No. 60/574,429, filed on May 25, 2004. Each of the aforementioned applications is incorporated by reference in its entirety herein.

FIELD OF THE INVENTION

The invention relates generally to an implantable device that could be used in the vasculature to treat common vascular malformations. More particularly, it relates to a flexible, biocompatible device that can be introduced into the vasculature of a patient to embolize and occlude aneurysms, particularly cerebral aneurysms.

BACKGROUND OF THE INVENTION

Walls of the vasculature, particularly arterial walls, may develop pathological dilatation called an aneurysm. Aneurysms are commonly observed as a ballooning-out of the wall of an artery. This is a result of the vessel wall being weakened by disease, injury or a congenital abnormality. Aneurysms have thin, weak walls and have a tendency to rupture and are often caused or made worse by high blood pressure. Aneurysms could be found in different parts of the body; the most common being abdominal aortic aneurysms (AAA) and the brain or cerebral aneurysms. The mere presence of an aneurysm is not always life-threatening, but they can have serious heath consequences such as a stroke if one should rupture in the brain. Additionally, as is known, a ruptured aneurysm can also result in death.

The most common type of cerebral aneurysm is called a saccular aneurysm, which is commonly found at the bifurcation of a vessel. The locus of bifurcation, the bottom of the V in the Y, could be weakened by hemodynamic forces of the blood flow. On a histological level, aneurysms are caused by damage to cells in the arterial wall. Damage is believed to be caused by shear stresses due to blood flow. Shear stress generates heat that breaks down the cells. Such hemodynamic stresses at the vessel wall, possibly in conjunction with intrinsic abnormalities of the vessel wall, have been considered to be the underlying cause for the origin, growth and rupture of these saccular aneurysms of the cerebral arteries (Lieber and Gounis, The Physics of Endoluminal stenting in the Treatment of Cerebrovascular Aneurysms, Neurol Res 2002: 24: S32-S42). In histological studies, damaged intimal cells are elongated compared to round healthy cells. Shear stress can vary greatly at different phases of the cardiac cycle, locations in the arterial wall and among different individuals as a function of geometry of the artery and the viscosity, density and velocity of the blood. Once an aneurysm is formed, fluctuations in blood flow within the aneurysm are of critical importance because they can induce vibrations of the aneurysm wall that contribute to progression and eventual rupture. For a more detailed description of the above concepts see, for example, Steiger, Pathophysiology of Development and Rupture of Cerebral Aneurysms, Acta Neurochir Suppl 1990: 48: 1-57; Fergueson, Physical Factors in the Initiation, Growth and Rupture of Human Intracranial Saccular Aneurysms, J Neurosurg 1972: 37: 666-677.

Aneurysms are generally treated by excluding the weakened part of the vessel from the arterial circulation. For treating a cerebral aneurysm, such reinforcement is done in many ways: (i) surgical clipping, where a metal clip is secured around the base of the aneurysm; (ii) packing the aneurysm with microcoils, which are small, flexible wire coils; (iii) using embolic materials to "fill" an aneurysm; (iv) using detachable balloons or coils to occlude the parent vessel that supplies the aneurysm; and (v) endovascular stenting. For a general discussion and review of these different methods see Qureshi, Endovascular Treatment of Cerebrovascular Diseases and Intracranial Neoplasms, Lancet. 2004 Mar. 6; 363 (9411):804-13; Brilstra et al. Treatment of Intracranial Aneurysms by Embolization with Coils: A Systematic Review, Stroke 1999; 30: 470-476.

As minimally invasive interventional techniques gain more prominence, microcatheter based approaches for treating neurovascular aneurysms are becoming more prevalent. Micro-catheters, whether flow-directed or wire-directed, are used for dispensing embolic materials, micro coils or other structures (e.g., stents) for embolization of the aneurysm. A microcoil can be passed through a microcatheter and deployed in an aneurysm using mechanical or chemical detachment mechanisms, or be deployed into the parent vessel to permanently occlude it and thus block flow into the aneurysm. Alternatively, a stent could be tracked through the neurovasculature to the desired location. Article by Pereira, History of Endovascular Aneurysms Occlusion in Management of Cerebral Aneurysms; Eds: Le Roux et al., 2004, pp: 11-26 provides an excellent background on the history of aneurysm detection and treatment alternatives.

As noted in many of the articles mentioned above, and based on the origin, formation and rupture of the cerebral aneurysm, it is obvious that the goal of aneurysmal therapy is to reduce the risk of rupture of the aneurysm and thus the consequences of sub-arachnoid hemorrhage. It should also be noted that while preventing blood from flowing into the aneurysm is highly desirable, so that the weakened wall of the aneurysm doesn't rupture, it may also be vital that blood flow to the surrounding structures is not limited by the method used to obstruct blood flow to the aneurysm. Conventional stents developed for treating other vascular abnormalities in the body are ill suited for embolizing cerebral aneurysms. This could lead to all the usual complications when high oxygen consumers, such as brain tissue, are deprived of the needed blood flow.

There are many shortcomings with the existing approaches for treating neurovascular aneurysms. The vessels of the neurovasculature are the most tortuous in the body; certainly more tortuous than the vessels of the coronary circulation. Hence, it is a challenge for the surgeon to navigate the neurovasculature using stiff coronary stents that are sometimes used in the neurovasculature for treating aneurysms. The bending force of a prosthesis indicates the maneuverability of the prosthesis through the vasculature; a lower bending force would imply that the prosthesis is more easily navigated through the vasculature compared to one with a higher bending force. Bending force for a typical coronary stent is 0.05 lb-in (force to bend 0.5 inches cantilever to 90 degree). Hence, it will be useful to have neural prosthesis that is more flexible than existing stents.

Existing stent structures, whether used in coronary vessels or in the neurovasculature (microcoils) are usually straight, often laser cut from a straight tubing or braiding with stiff metallic materials. However, most of the blood vessels are curved. Hence, current stent structures and microcoils impart significant stress on the vessel walls as they try to straighten a curved vessel wall. For a weakened vessel wall, particularly where there is a propensity for an aneurysm formation, this could have disastrous consequences.

As noted earlier, the hemodynamic stress placed on the blood vessels, particularly at the point of bifurcation, leads to weakening of the vessel walls. The most significant source of such stress is the sudden change in direction of the blood flow. Hence, if one were to minimize the sudden change in direction of blood flow, particularly at the location of vessel weakness, it would be beneficial.

Existing approaches to occluding aneurysms could lead to another set of problems. Methods that merely occlude the aneurysm by packing or filling it with embolic material (coils or liquid polymers) do not address the fundamental flow abnormalities that contribute to the formation of aneurysm.

Currently, many different stent structures and stent deployment methods exist. A stent structure could be expanded after being placed intraluminally on a balloon catheter. Alternatively, self-expanding stems could be inserted in a compressed state and expanded upon deployment. All the stents need to have the radial rigidity to maintain patency of the lumen and simultaneously have the longitudinal flexibility to facilitate navigating the tortuous path of the vasculature. For balloon expandable stents, the stent is mounted on a balloon at the distal end of a catheter, the catheter is advanced to the desired location and the balloon is inflated to expand the stent into a permanent expanded condition. The balloon is then deflated and the catheter withdrawn leaving the expanded stent to maintain vessel patency. Because of the potentially lethal consequences of dissecting or rupturing an intracerebral vessel, the use of balloon expandable stents in the brain is fraught with problems. Proper deployment of a balloon expandable stent requires slight over expanding of the balloon mounted stent to embed the stent in the vessel wall and the margin of error is small. Balloon expandable stents are also poorly suited to adapt to the natural tapering of cerebral vessels which taper proximally to distally. If a stent is placed from a parent vessel into a smaller branch vessel the change in diameter between the vessels makes it difficult to safely deploy a balloon expandable stent. A self-expanding stent, where the compressed or collapsed stent is held by an outer restraining sheath over the compressed stent to maintain the compressed state until deployment. At the time of deployment, the restraining outer sheath is retracted to uncover the compressed stent, which then expands to keep the vessel open. Additionally, the catheters employed for delivering such prosthesis are micro-catheters with outer diameter of 0.65 mm to 1.3 mm compared to the larger catheters that are used for delivering the large coronary stents to the coronaries.

Various stent structures and solutions have been suggested for treating cerebral aneurysms. U.S. Pat. No. 6,669,719 (Wallace et al.) describes a stent and a stent catheter for intra-cranial use. A rolled sheet stent is releasably mounted on the distal tip of a catheter. Upon the rolled sheet being positioned at the aneurysm, the stent is released. This results in immediate and complete isolation of an aneurysm and surrounding side branches of the circulatory system and redirecting blood flow away from the aneurysm. A significant drawback of such a system is that the surrounding side branches, along with the target aneurysm, are deprived of the needed blood flow after the stent has been deployed.

U.S. Pat. No. 6,605,110 (Harrison) describes a self-expanding stent for delivery through a tortuous anatomy or for conforming the stent to a curved vessel. This patent describes a stent structure with radially expandable cylindrical elements arranged in parallel to each other and interspersed between these elements and connecting two adjacent cylindrical elements are struts that are bendable. While this structure could provide the necessary flexibility and bendability of the stent for certain applications, it is expensive and complex to manufacture.

U.S. Pat. No. 6,572,646 (Boylan) discloses a stent made up of a super-elastic alloy, such as Ni—Ti alloy (Nitinol), with a low temperature phase that induces a first shape to the stent and a high temperature phase that induces a second shape to the stent with a bend along the length. U.S. Pat. No. 6,689,162 (Thompson) discloses a braided prosthesis that uses strands of metal, for providing strength, and compliant textile strands. The objective of Thompson is to have a prosthesis that combines the structural strength and resiliency of a self-expanding stent and the low permeability of a graft. U.S. Pat. No. 6,656,218 (Denardo et al.) describes an intravascular flow modifier that allows microcoil introduction even after placing the modifier.

SUMMARY OF THE INVENTION

An aspect of the present invention provides a highly flexible implantable occluding device that can easily navigate the tortuous vessels of the neurovasculature. Additionally, occluding device can easily conform to the shape of the tortuous vessels of the vasculature. Furthermore, the occluding device can direct the blood flow within a vessel away from an aneurysm; additionally such an occluding device allows adequate blood flow to be provided to adjacent structures such that those structures, whether they are branch vessels or oxygen demanding tissues, are not deprived of the necessary blood flow.

The occluding device is also capable of altering blood flow to the aneurysm, yet maintaining the desired blood flow to the surrounding tissue and within the vessel. In this instance, some blood is still allowed to reach the aneurysm, but not enough to create a laminar flow within the aneurysm that would cause injury to its thinned walls. Instead, the flow would be intermittent, thereby providing sufficient time for blood clotting or filler material curing within the aneurysm.

The occluding device is flexible enough to closely approximate the native vasculature and conform to the natural tortuous path of the native blood vessels. One of the significant attributes of the occluding device according to the present invention is its ability to flex and bend, thereby assuming the shape of a vasculature within the brain. These characteristics are for a neurovascular occluding device than compared to a coronary stent, as the vasculature in the brain is smaller and more tortuous.

In general terms, aspects of the present invention relate to methods and devices for treating aneurysms. In particular, a method of treating an aneurysm with a neck comprises deploying a vascular occluding device in the lumen of a vessel at the location of the aneurysm, whereby the blood flow is redirected away from the neck of the aneurysm. The induced stagnation of the blood in the lumen of the aneurysm would create embolization in the aneurysm. The occluding device spans the width of the stem of the aneurysm such that it obstructs or minimizes the blood flow to the aneurysm. The occluding device is very flexible in both its material and its arrangement. As a result, the occluding device can be easily navigated through the tortuous blood vessels, particularly those in the brain. Because the occluding device is flexible, very little force is required to deflect the occluding device to navigate through the vessels of the neurovasculature, which is of significance to the operating surgeon.

A significant feature of the occluding device, apart from its flexibility, is that the occluding device may have an asymmetrical braid pattern with a higher concentration of braid strands or a different size of braid strands on the surface facing the neck of the aneurysm compared to the surface radially opposite to it. In one embodiment, the surface facing the aneurysm is almost impermeable and the diametrically opposed surface is highly permeable. Such a construction would direct blood flow away from the aneurysm, but maintain blood flow to the side branches of the main vessel in which the occluding device is deployed.

In another embodiment, the occluding device has an asymmetrical braid count along the longitudinal axis of the occluding device. This provides the occluding device with a natural tendency to curve, and hence conform to the curved blood vessel. This reduces the stress exerted by the occluding device on the vessel wall and thereby minimizing the chances of aneurysm rupture. Additionally, because the occluding device is naturally curved, this eliminates the need for the tip of the micro-catheter to be curved. Now, when the curved occluding device is loaded on to the tip of the micro-catheter, the tip takes the curved shape of the occluding device. The occluding device could be premounted inside the micro-catheter and can be delivered using a plunger, which will push the occluding device out of the micro-catheter when desired. The occluding device could be placed inside the micro-catheter in a compressed state. Upon exiting the micro-catheter, it could expand to the size of the available lumen and maintain patency of the lumen and allow blood flow through the lumen. The occluding device could have a lattice structure and the size of the openings in the lattice could vary along the length of the occluding device. The size of the lattice openings can be controlled by the braid count used to construct the lattice.

According to aspects of the invention, the occluding device can be used to remodel an aneurysm within the vessel by, for example, neck reconstruction or balloon remodeling. The occluding device can be used to form a barrier that retains occlusion material such as a well known coil or viscous fluids, such as "ONYX" by Microtherapeutics, within the aneurysm so that introduced material will not escape from within the aneurysm due to the lattice density of the occluding device in the area of the aneurysm.

In another aspect of this invention, a device for occluding an aneurysm is disclosed. The device is a tubular with a plurality of perforations distributed on the wall of the member. The device is placed at the base of the aneurysm covering the neck of the aneurysm such that the normal flow to the body of the aneurysm is disrupted and thereby generating thrombus and ultimately occlusion of the aneurysm.

In yet another aspect of this invention, the device is a braided tubular member. The braided strands are ribbons with rectangular cross section, wires with a circular cross section or polymeric strands.

In another embodiment, a device with a braided structure is made in order to conform to a curved vessel in the body, where the density of the braid provides enough rigidity and radial strength. Additionally, the device can be compressed using a force less than 10 grams. This enables the device to be compliant with the artery as the arterial wall is pulsating. Also, the device is capable of bending upon applying a force of less than 5 gram/cm.

Other aspects of the invention include methods corresponding to the devices and systems described herein.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 1 is an illustration of an aneurysm, branch vessels and blood flow to the aneurysm.

FIGS. 2A and 2B illustrate one embodiment of an occluding device to treat aneurysms.

FIG. 4A is another embodiment of an occluding device for treating aneurysms.

FIGS. 4B and 4C illustrate cross sections of portions of ribbons that can be used to form the occluding device of FIG. 4A.

FIG. 5 shows the occluding device in a compressed state inside a micro-catheter being advanced out of the micro-catheter using a plunger.

FIG. 6 shows the compressed occluding device shown in FIG. 5 deployed outside the micro-catheter and is in an expanded state.

DETAILED DESCRIPTION OF THE PREFERRED EMBODIMENTS

Figure 3:
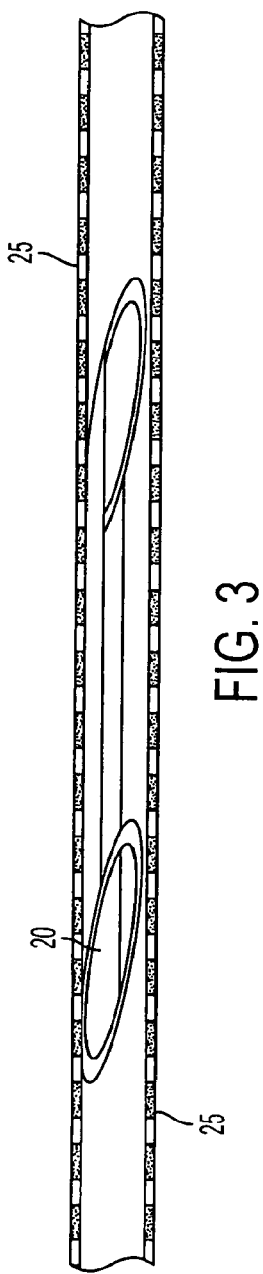
FIG. 3 is an illustration of the embodiment shown in FIG. 2 in a compressed state inside a micro-catheter.

The devices shown in the accompanying drawings are intended for treating aneurysms. They are generally deployed, using micro-catheters, at the location of a cerebral aneurysm that is intended to be treated. One such system is disclosed in copending U.S. patent application titled "System and Method for Delivering and Deploying an Occluding Device Within a Vessel", U.S. application Ser. No. 11/136, 398, filed on May 25, 2005, which is incorporated herein by reference in its entirety. The embodiments of the endovascular occluding device according to aspects of the present invention is useful for treating cerebral aneurysms that are commonly treated using surgical clips, microcoils or other embolic devices.

FIG. 1 illustrates a typical cerebral aneurysm 10 in the brain. A neck 11 of the aneurysm 10 can typically define an opening of between about 2 to 25 mm. As is understood, the neck 11 connects the vessel 13 to the lumen 12 of the aneurysm 10. As can be seen in FIG. 1, the blood flow 1 within the vessel 13 is channeled through the lumen 12 and into the aneurysm. In response to the constant blood flow into the aneurysm, the wall 14 of lumen 12 continues to distend and presents a significant risk of rupturing. When the blood within the aneurysm 10 causes pressure against the wall 14 that exceeds the wall strength, the aneurysm ruptures. The present invention could prevent such ruptures. Also shown in FIG. 1 are the bifurcation 15 and the side branches 16.

FIG. 2 illustrates one embodiment of an vascular occluding device 20 in accordance with an aspect of the present invention. In the illustrated embodiment, the occluding device 20 has a substantially tubular structure 22 defined by an outer surface 21, an inner surface 24 and a thin wall that extends between the surfaces 21, 24. A plurality of openings 23 extend between the surfaces 21, 24 and allow for fluid flow from the interior of the occluding device 20 to the wall of the vessel. Occluding device 20 is radially compressible and longitudinally adjustable.

FIG. 3 shows a micro-catheter 25 and the occluding device 20 inside the microcatheter 25 in a compressed state prior to being released within the vasculature of the patient.

FIG. 4 illustrates another embodiment of the occluding device 30 having two or more strands of material(s) 31, 32 wound in a helical fashion. The braiding of such material in this fashion results in a lattice structure 33. As can be understood, the dimension of the lattice 33 and the formed interstices 34 is determined, at least in part, by the thickness of the strand materials, the number of strands and the number of helices per unit length of the occluding device 30.

The occluding device 30 is radially compressible and radially expandable without the need for supplemental radially expanding force, such as an inflatable balloon. The occluding device 30 is constructed by winding the two strands (31, 32 in opposite directions. In an embodiment, the strands 31, 32 are in the shape of rectangular ribbon (See FIG. 4C). The ribbons can be formed of known flexible materials including shape memory materials, such as Nitinol, platinum and stainless steel.

Figure 7:
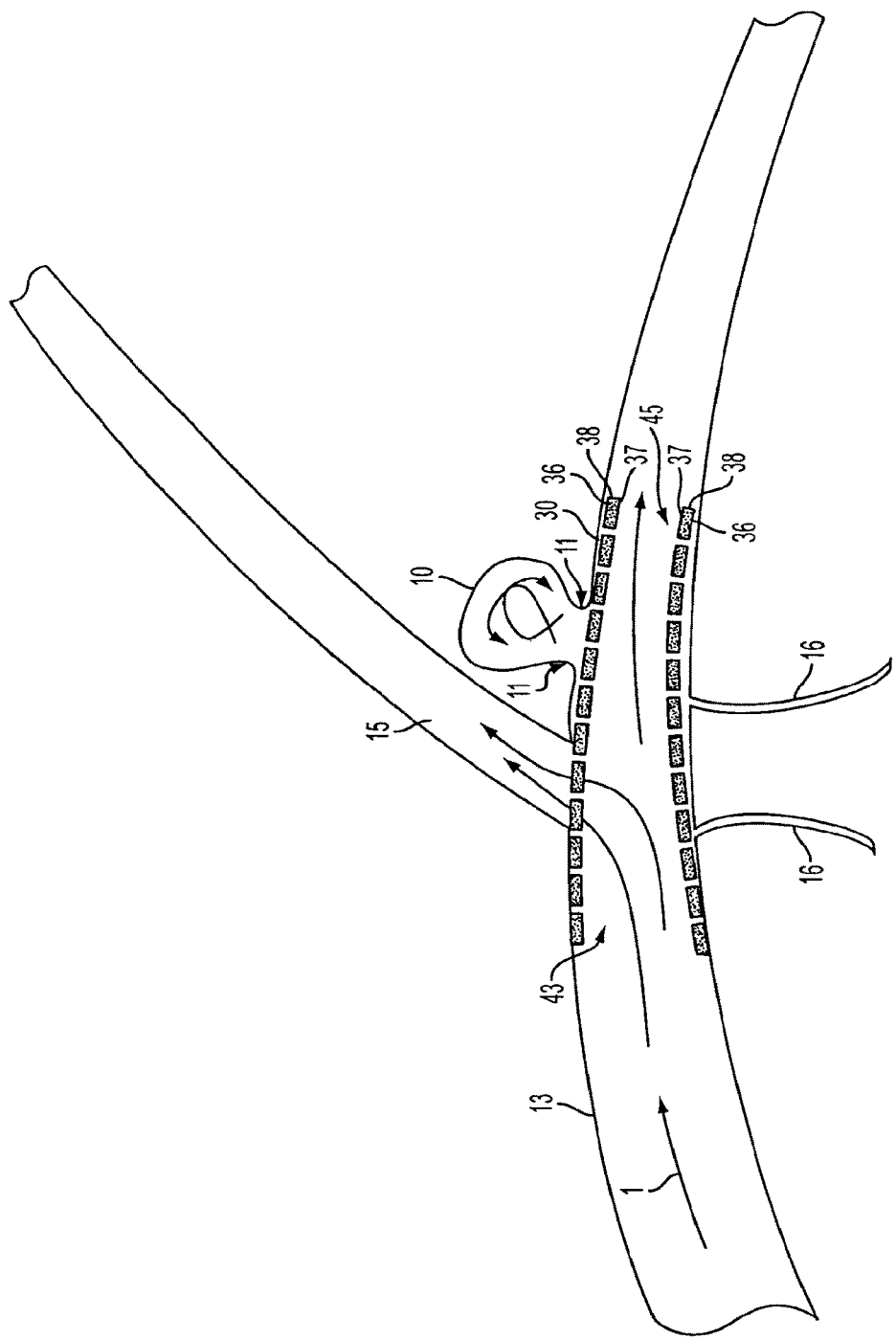
FIG. 7 shows the deployed occluding device inside the lumen of a vessel spanning the neck of the aneurysm, a bifurcation and branch vessels.

The ribbon used as the braiding material for the strands 31, 32 can include a rectangular cross section 35 (FIG. 4C). As shown in FIGS. 4C and 7, the surface 36 that engages an inner surface of the vessel has a longer dimension (width) when compared to the wall 38 that extends between the surfaces 36, 37 (thickness). A ribbon with rectangular cross section has a higher recovery (expansive) force for the same wall thickness when compared to a wire with a circular (round) cross section. Additionally, a flat ribbon allows for more compact compression of the occluding device 20 and causes less trauma to the vascular wall when deployed because it distributes the radial expansion forces over a greater surface area. Similarly, flat ribbons form a more flexible device for a given lattice density because their surface area (width) is greater for a given thickness in comparison to round wire devices.

While the illustrated embodiment discloses a ribbon having a rectangular cross section in which the length is greater than its thickness, the ribbon for an alternative embodiment of the disclosed occluding devices may include a square cross section. In another alternative embodiment, a first portion of the ribbon may include a first form of rectangular cross section and a second portion 39 of the ribbon (FIG. 4B) may include a round, elliptical, oval or alternative form of rectangular cross section. For example, end sections of the ribbons may have substantially circular or oval cross section and the middle section of the ribbons could have a rectangular cross section.

In an alternative embodiment, the occluding device 30 can be formed by winding more than two strands of ribbon. In an embodiment, the occluding device 30 could include as many as sixteen strands of ribbon. By using standard techniques employed in making radially expanding stents, one can create an occluding device 30 with interstices 34 that are larger than the thickness of the ribbon or diameter of the wire. The ribbons can have different widths. In such an embodiment, the different ribbon(s) can have different width(s) to provide structure support to the occluding device 30 and the vessel wall. The ribbons according to the disclosed embodiments can also be formed of different materials. For example, one or more of the ribbons can be formed of a biocompatible metal material, such as those disclosed herein, and one or more of the ribbons can be formed of a biocompatible polymer.

FIG. 5 shows the intravascular occluding device 30 in a radially compressed state located inside the micro-catheter 25. In one embodiment, the occluding device 30 could be physically attached to the catheter tip. This could be accomplished by constraining the occluding device 30 in the distal segment of the micro-catheter. The micro-catheter 25 is slowly advanced over a guidewire (not shown) by a plunger 50 and when the tip of the micro-catheter 25 reaches the aneurysm, the occluding device is released from the tip. The occluding device 30 expands to the size of the vessel and the surface of the occluding device 30 is now apposed to the vessel wall 15 as shown in FIG. 6. Instruments and methods for delivering and deploying the occluding device 30 are disclosed in the above-referenced copending application.

With reference to FIG. 7, the occluding device 30 is deployed inside the lumen of a cerebral vessel 13 with an aneurysm 10. During its deployment, the proximal end 43 of the occluding device 30 is securely positioned against the lumen wall of the vessel 13 before the bifurcation 15 and the distal end 45 of the occluding device 30 is securely positioned against the lumen wall of the vessel 13 beyond the neck 11 of aneurysm 10. After the occluding device 30 is properly positioned at the desired location within the vessel 13 (for example, see FIG. 7), flow inside the lumen of aneurysm 10 is significantly minimized while the axial flow within the vessel 13 is not significantly compromised, in part due to the minimal thickness of the walls 38.

The flow into the aneurysm 10 will be controlled by the lattice density of the ribbons and the resulting surface coverage. Areas having greater lattice densities will have reduced radial (lateral) flow. Conversely, areas of lesser lattice densities will allow significant radial flow through the occluding device 30. As discussed below, the occluding device 30 can have longitudinally extending (lateral) areas of different densities. In each of these areas, their circumferential densities can be constant or vary. This provides different levels of flow through adjacent lateral areas. The location within a vessel of the areas with greater densities can be identified radiographically so that the relative position of the occluding device 30 to the aneurysm 10 and any vascular branches 15, 16 can be determined. The occluding device 30 can also include radiopaque markers.

Figure 8:
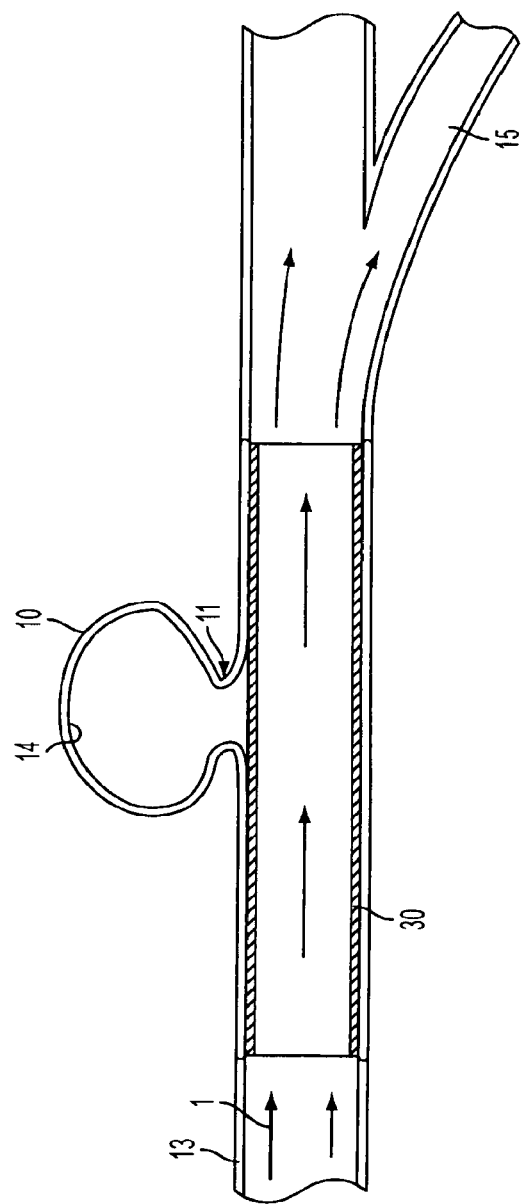
FIG. 8 is a schematic showing the occluding device located in the lumen of a vessel and the change in the direction of the blood flow.

The reduction of blood flow within the aneurysm 10 results in a reduction in force against the wall 14 and a corresponding reduction in the risk of vascular rupturing. When the force and volume of blood entering the aneurysm 10 is reduced by the occluding device, the laminar flow into the aneurysm 10 is stopped and the blood within the aneurysm begins to stagnate. Stagnation of blood, as opposed to continuous flow through the lumen 12 of the aneurysm 10, results in thrombosis in the aneurysm 10. This also protects the aneurysm from rupturing. Additionally, due to the density of the portion of the occluding device 30 at the bifurcation 15, the openings (interstices) 34 in the occluding device 30 allow blood flow to continue to the bifurcation 15 and the side branches 16 of the vessel. If the bifurcation 15 is downstream of the aneurysm, as shown in FIG. 8, the presence of the occluding device 30 still channels the blood away from the aneurysm 10 and into the bifurcation 15.

Figure 9:
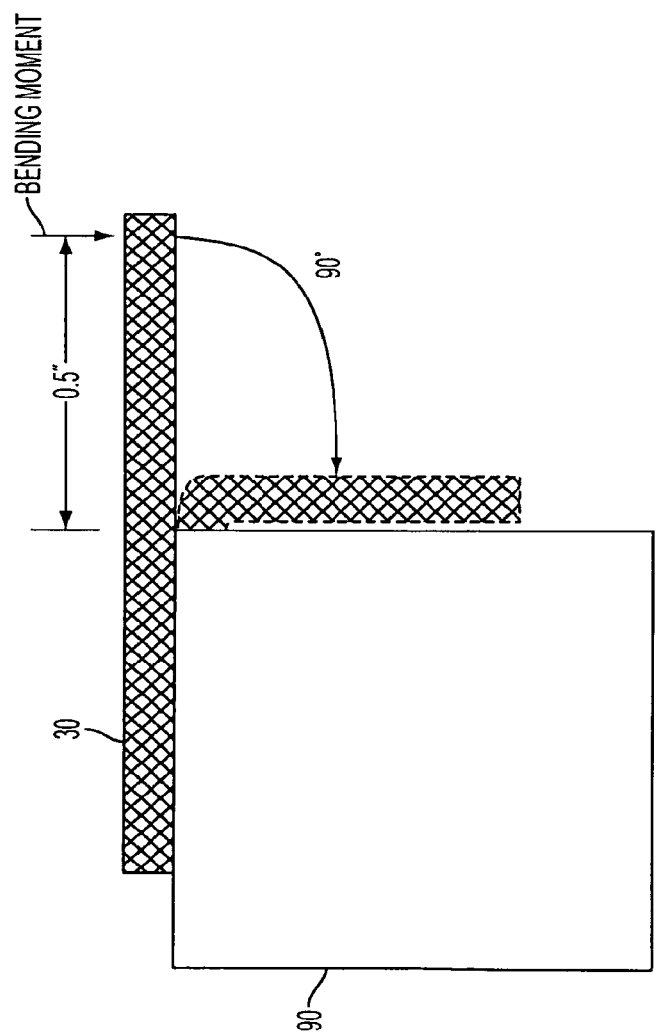
FIG. 9 shows the effect of a bending force on a conventional stent compared to the occluding device of the present invention.

The occluding devices described herein have the flexibility necessary to conform to the curvature of the vasculature. This is in contrast to coronary stents that cause the vasculature to conform essentially to their shape. The ability to conform to the shape of the vasculature is more significant for neurovascular occluding devices than coronary stents, as the vasculature in the brain is smaller and more tortuous. Tables 1 and 2 demonstrate these characteristics of the claimed neurovascular occluding device. To demonstrate that the disclosed occluding devices exhibit very desirable bending characteristics, the following experiment was performed. The occluding device made by the inventors was set on a support surface 90 as shown in FIG. 9. About 0.5 inches of the occluding device 30 was left unsupported. Then, a measured amount of force was applied to the unsupported tip until the occluding device was deflected by 90 degrees from the starting point. A similar length of a commercially available coronary stent was subjected to the same bending moment. The results are shown in Table 1. Similar to the reduced compressive force, the occluding device of the present invention required an order of magnitude lower bending moment (0.005 lb-in compared to 0.05 lb-in for a coronary stent).

TABLE 1

Bending Force Required to Bend a 0.5"
Cantilever Made by the Occlusion Device

| | | |
|---|---|---|
| Coronary stent | commercially available stent | 0.05 lb-in |
| Neurovascular | Occluding Device (30) | 0.005 lb-in |

The occluding devices according to the present invention also provides enhanced compressibility (i.e., for a given force how much compression could be achieved or to achieve a desired compression how much force should be exerted) compared to coronary stents. An intravascular device that is not highly compressible is going to exert more force on the vessel wall compared to a highly compressible device. This is of significant clinical impact in the cerebral vasculature as it is detrimental to have an intravascular device that has low compressibility.

TABLE 2

Figure 10:
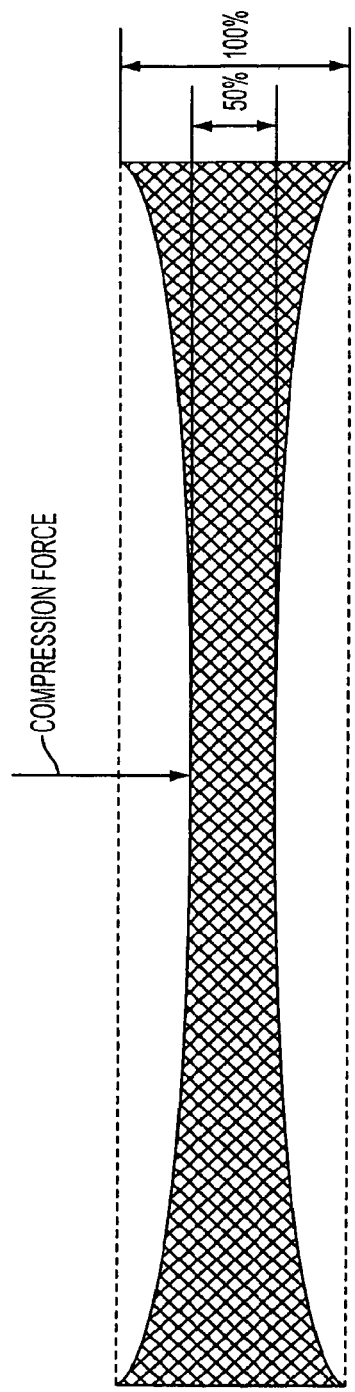
FIG. 10 demonstrates the flexibility of the current invention, compared to a traditional stent, by the extent of the deformation for an applied force.

Compressive Force Required to Compress the Occluding
device to 50% of the Original Diameter (see FIG. 10)

| | | |
|---|---|---|
| Coronary stem | (commercially available | 0.2 lb |
| Neurovascular | Occluding device (30) | 0.02 lb |

Figure 11:
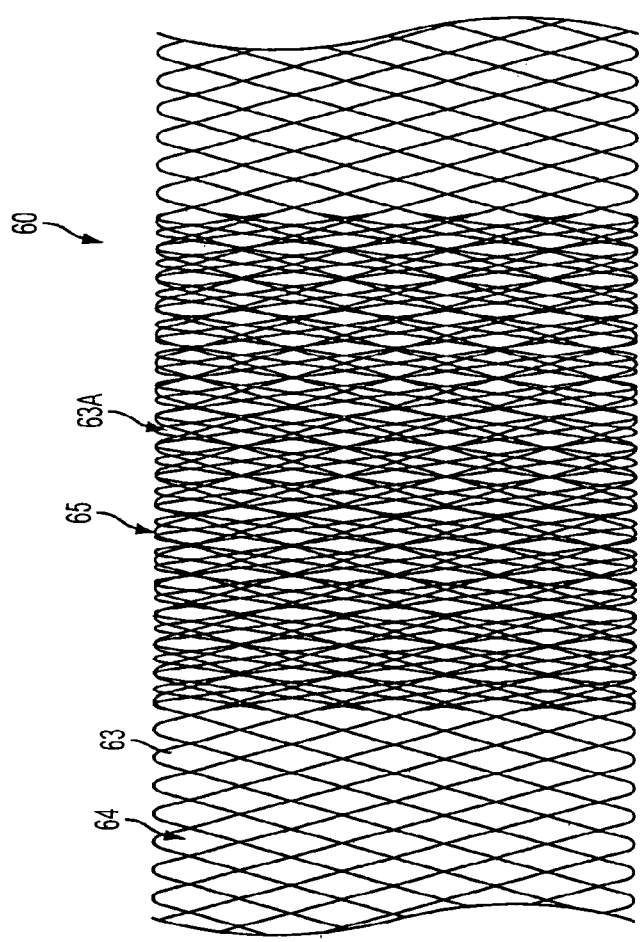
FIG. 11 shows the non-uniform density of the braid that provides the desired curved occluding device.
Figure 12:
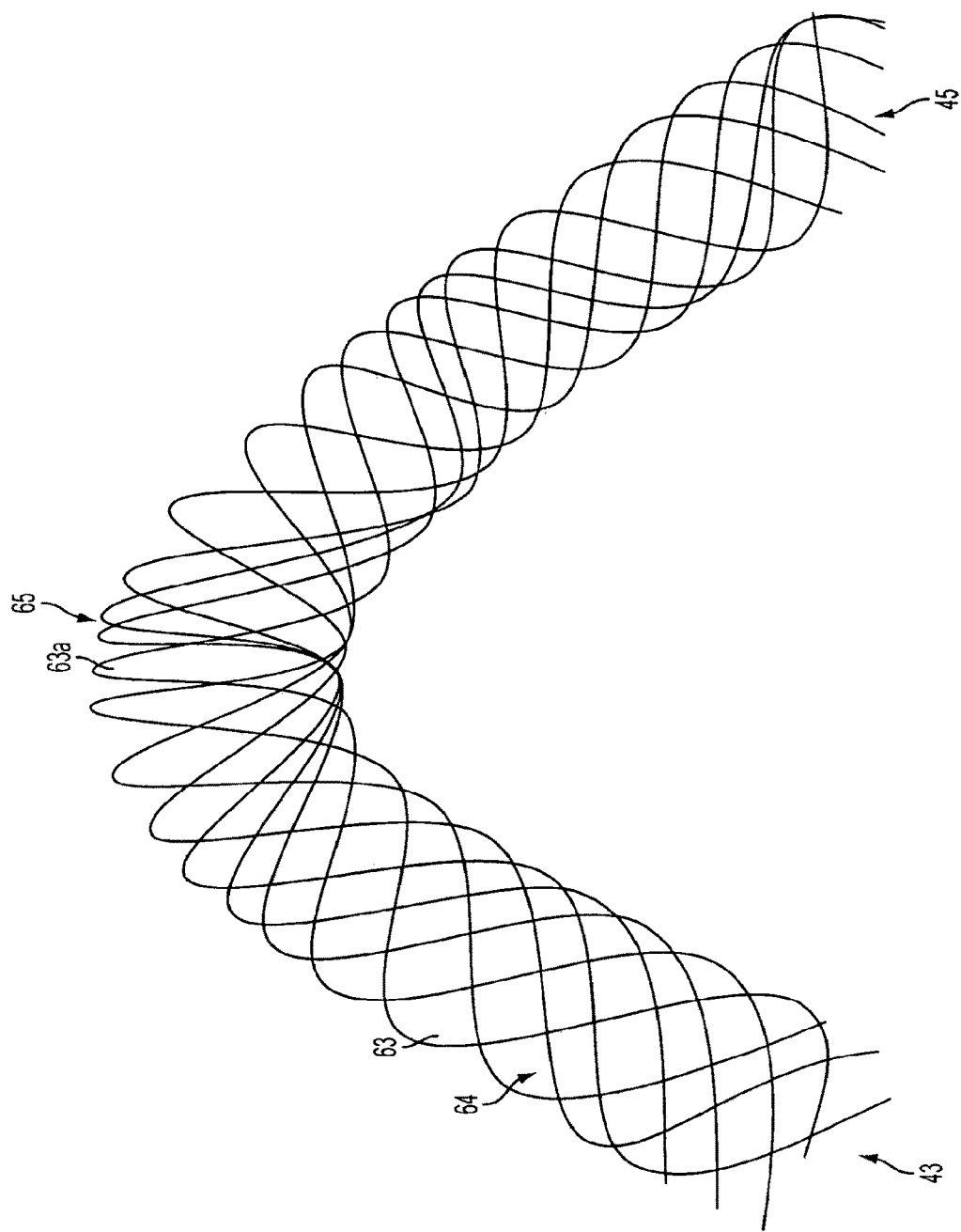
FIG. 12 illustrates the difference in lattice density or porosity due to the non-uniform density of the braiding of the occluding device.
Figure 13:
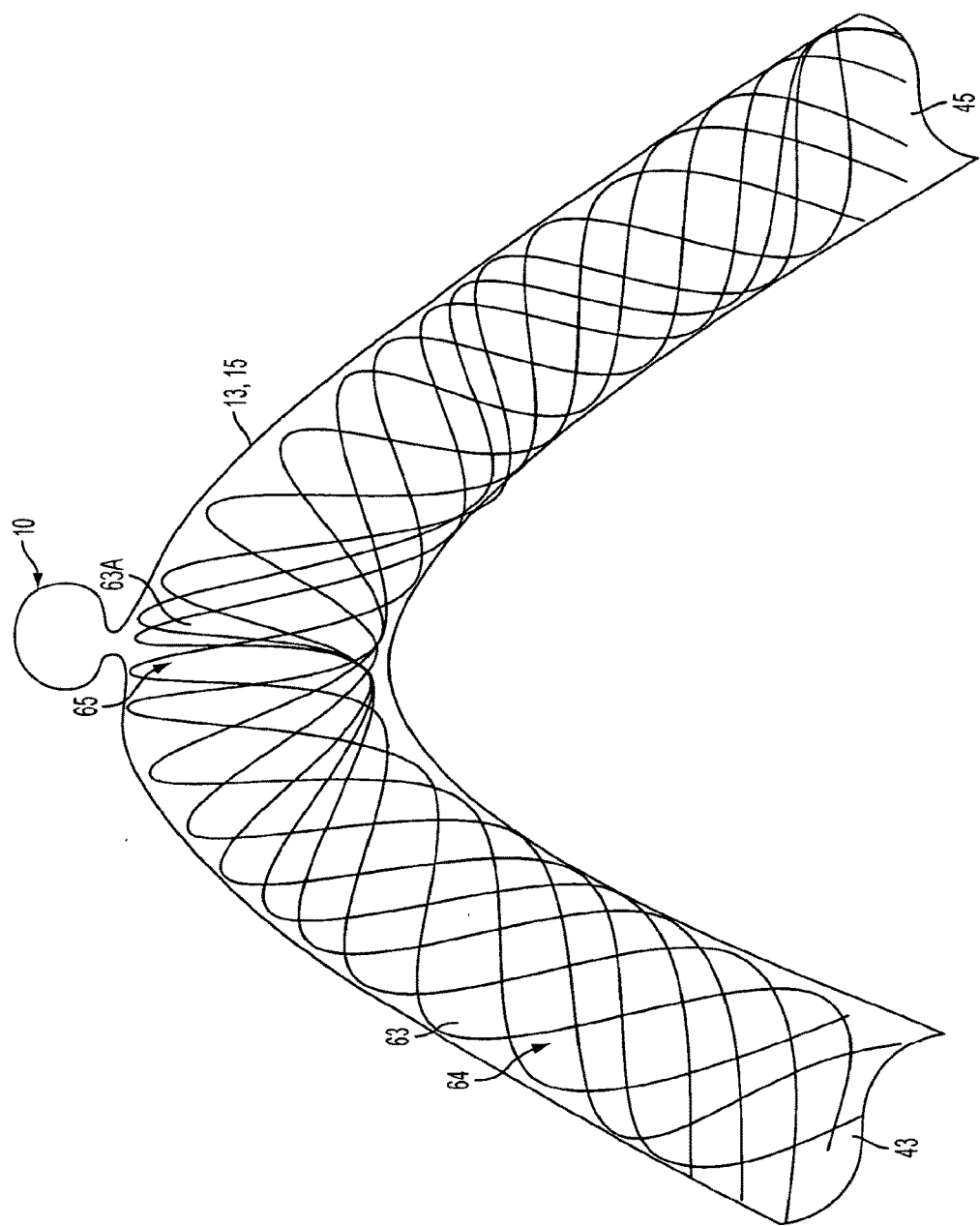
FIG. 13 shows the varying lattice density occluding device covering the neck of an aneurysm.

FIGS. 11-13 show an embodiment of the occluding device 60 in which the lattice structure 63 of the occluding device 60 is non-uniform across the length of the occluding device 60. In the mid-section 65 of the occluding device 60, which is the section likely to be deployed at the neck of the aneurysm, the lattice density 63a is intentionally increased to a value significantly higher than the lattice density elsewhere in the occluding device 60. For example, as seen in FIG. 11, lattice density 63A is significantly higher than the lattice density 63 in adjacent section 64. At one extreme, the lattice density (porosity provided by the interstices) could be zero, i.e., the occluding device 60 is completely impermeable. In another embodiment, the lattice density 63A in mid-section 65 could be about 50%, while the lattice density in the other sections 64 of the occluding device is about 25%. FIG. 12 shows such the occluding device 60 in a curved configuration and FIG. 13 shows this occluding device 60 deployed in the lumen of a vessel. FIG. 13 also illustrates the part of the occluding device 60 with increased lattice density 63A positioned along the neck of aneurysm 10. As with any of the disclosed occluding devices, the lattice density of at least one portion of occluding device 60 can be between about 20% and about 80%. The lattice density of these embodiments could be between about 25% and about 50%.

Figure 14:
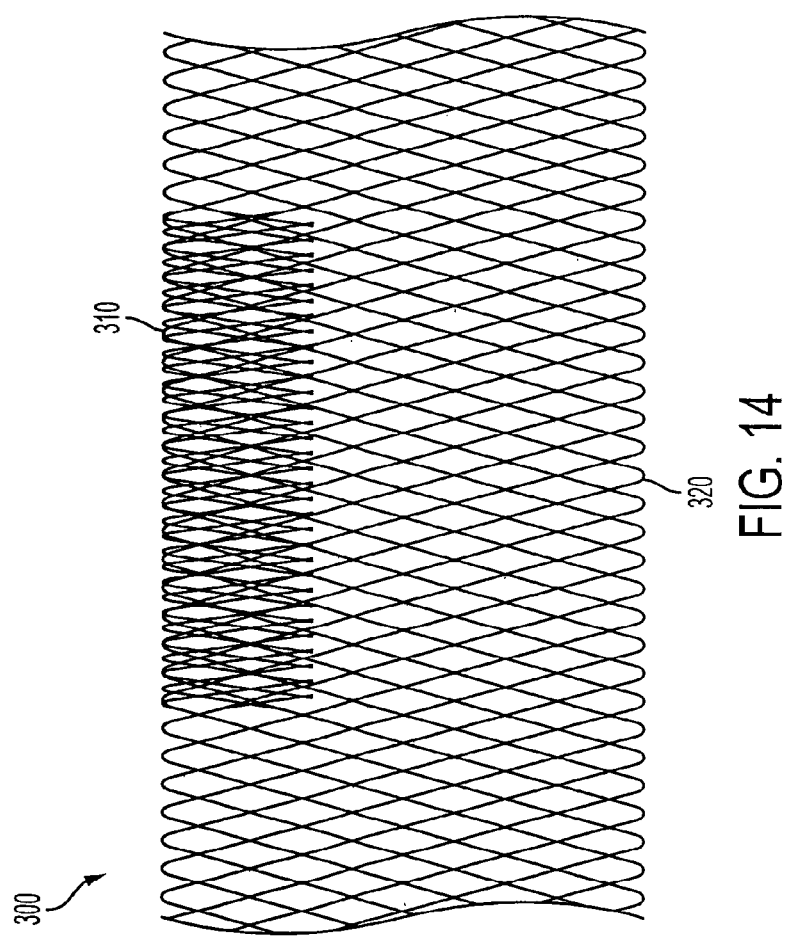
FIGS. 14 and 15 show an embodiment of the vascular occluding device where the lattice density is asymmetrical about the longitudinal axis near the aneurysm neck.
Figure 15:
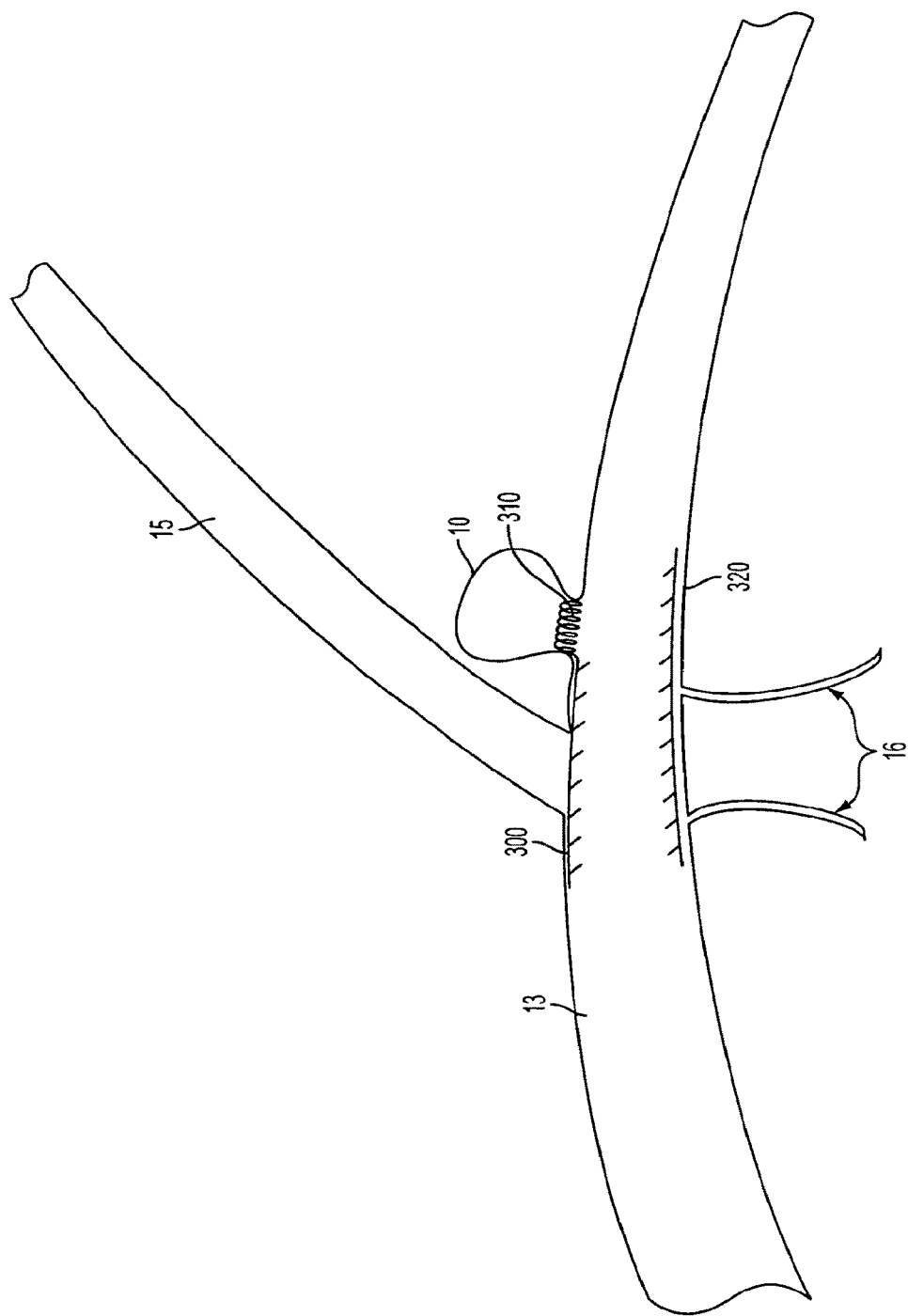

Another embodiment of the occluding device 300 is shown in FIGS. 14 and 15. In this embodiment, the occluding device 300 is deployed in lumen of a vessel with an aneurysm. The occluding device 300 includes a surface 310 that faces the lumen of the aneurysm. This surface 310 has a significantly higher lattice density (smaller and/or fewer interstices) compared to the diametrically opposite surface 320. Due to the higher lattice density of surface 310, less blood flows into the lumen of the aneurysm. However, there is no negative impact on the blood flow to the side branches as the lattice density of the surface 320 facing the side branches is not reduced.

Figure 16:
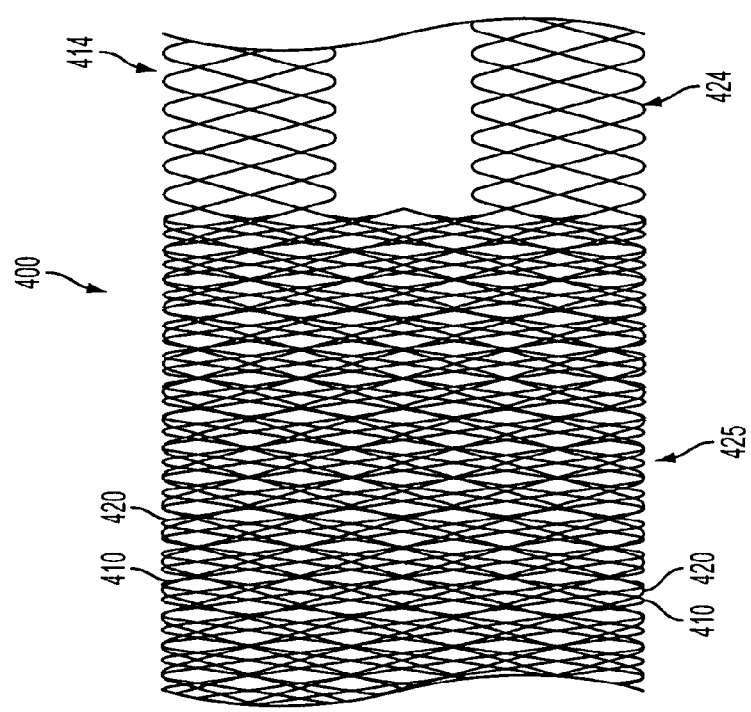
FIG. 16 illustrates a bifurcated occluding device according to an embodiment of the present invention in which two occluding devices of lesser densities are combined to form a single bifurcated device.

Any of the occluding devices disclosed herein can be used with a second occluding device to create a bifurcated occluding device 400 as shown in FIG. 16. This device could be created in vivo. In forming the occluding device 400, a portion of a first occluding device 410 having a low density can be combined with a portion of a second occluding device 410 that also has a low density. The occluding devices 410, 420 can be any of those discussed herein. After these portions of the two occluding devices 410, 420 are combined in an interwoven fashion to form an interwoven region 425, the remaining portions 414, 424 can branch off in different directions, thereby extending along two braches of the bifurcation. Areas outside of the interwoven region 425 can have greater lattice density for treating an aneurysm or lesser lattice density for allowing flow to branches 15, 16 of the vessel.

The density of the lattice for each of the disclosed occluding devices can be about 20% to about 80% of the surface area of its occluding device. In an embodiment, the lattice density can be about 20% to about 50% of the surface area of its occluding device. In yet another embodiment, the lattice density can be about 20% to about 305 of the surface area of its occluding device.

A typical occluding device having sixteen strand braids with 0.005 inch wide ribbon, 30 picks per inch (PPI) (number of crosses/points of contact per inch), and 0.09 inch outer diameter has approximately 30% of lattice density (surface covered by the ribbon). In the embodiments disclosed herein, the ribbon can be about 0.001 inch thick with a width of between about 0.002 inch to about 0.005 inch. In an embodiment, the ribbon has a thickness of about 0.004 inch. For a 16-strands ribbon that is about 0.001 inch thick and about 0.004 inch wide, the coverage for 50 PPI, 40 PPI, and 30 PPI will have 40%, 32% and 24% approximate surface coverage, respectively. For a 16-strands ribbon that is about 0.001 inch thick and about 0.005 inch wide, the coverage for 50 PPI, 40 PPI, and 30 PPI will be about 50%, 40% and 30% approximate surface coverage, respectively.

In choosing a size for the ribbon, one must consider that, when the ribbons are bundled up, will they traverse through a micro-catheter. For example, sixteen strands of a 0.006 inch wide ribbon may not pass through a micro-catheter having an internal diameter of 0.027 inch or less. However, as the width of ribbons become smaller, the recovery strength may decrease proportionally.

While other strand geometry may be used, these other geometries, such as round, will limit the device due to their thickness dimension. For example, a round wire with a 0.002 inch diameter will occupy up to 0.008 inch in cross sectional space within the vessel. This space can impact and disrupt the blood flow through the vessel. The flow in the vessel can be disrupted with this change in diameter.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents. Furthermore, no element, component or method step is intended to be dedicated to the public regardless of whether the element, component or method step is explicitly recited in the claims.

In the claims, reference to an element in the singular is not intended to mean "one and only one" unless explicitly stated, but rather is meant to mean "one or more." In addition, it is not necessary for a device or method to address every problem that is solvable by different embodiments of the invention in order to be encompassed by the claims.

What is claimed is:

1. A method, comprising:
expanding, from a delivery catheter, a device to an expanded state within a blood vessel, the device comprising a plurality of strands forming a lattice structure along the length of the device;
wherein, while in the expanded state, the density of the lattice structure is between about 25 to about 50 picks per inch, the plurality of strands form a plurality of openings extending between adjacent strands of the device, outer surfaces of the plurality of strands comprising between about 20 percent to about 50 percent of a total circumferential area of the device; the device being configured to bend 90 degrees about a fulcrum upon application of a bending moment of 0.005 lb-in to the device, and the device being configured to be compressed to 50% of an original diameter of the device upon application of a force of less than 10 grams.

2. The method of claim 1, wherein the openings occupy between about 50 to about 80 percent of the total circumferential area of the device.

3. The method of claim 1, further comprising adjusting the length of the device after the device is loaded within the delivery catheter.

4. The method of claim 1, wherein the expanding comprises aligning regions of the device proximate a branch or feeder portion of the vessel, the regions having a lesser lattice density relative to a region positioned proximate an aneurysm.

5. The method of claim 1, wherein, while in the expanded state, at least two of the strands have different cross-sectional dimensions.

6. The method of claim 1, wherein at least two of the strands are of different metallic materials.

7. The method of claim 1, wherein at least some of the strands comprise platinum.

8. The method of claim 1, wherein the strands are round in cross section.

9. A method, comprising:
expanding, from a delivery catheter, a device to an expanded state within a blood vessel, the device comprising a braided pattern of strands;
wherein, while in the expanded state, outer surfaces of the strands form between about 20 percent to about 50 percent of a total circumferential area of the device; the density of the braided pattern of strands is between about 25 to about 50 picks per inch, the device, upon application of a bending moment of 0.005 lb-in, is configured to bend 90 degrees about a longitudinal axis of the device, and the device is configured to be compressed to 50% of an original diameter of the device upon application of a force of less than 10 grams.

10. The method of claim 9, wherein a first portion of the braided pattern allows a first amount of radial blood flow to pass there through and a second portion of the braided pattern allows a second amount of radial blood flow there through, the first amount being greater than the second amount; wherein the first and second portions have different lattice densities.

11. The method of claim 9, further comprising adjusting the length of the device after the device is loaded within the delivery catheter.

12. The method of claim 9, wherein at least two of the strands have different cross-sectional dimensions.

13. The method of claim 9, wherein at least two of the strands are of different metallic materials.

14. The method of claim 9, wherein at least some of the strands comprise platinum.

15. The method of claim 9, wherein the strands are round in cross section.

16. A method comprising:
expanding, from a delivery catheter, a device from a compressed cross-sectional measurement in a compressed state to an expanded cross-sectional measurement, greater than the compressed cross-sectional measurement, in an expanded state within a blood vessel, the device comprising a braided pattern of strands;

wherein, while in the expanded state, outer surfaces of the strands comprise between about 20 percent to about 50 percent of a total circumferential area of the device, the strands form a lattice structure along the length of the device, the density of the lattice structure is between about 25 to about 50 picks per inch, a first portion of the elongate structure deflects 90 degrees about a fulcrum and relative to a second portion of the elongate structure when a bending moment of 0.005 lb-in is applied to the first portion, and the elongate structure is configured to be compressed to 50% of an original diameter of the device upon application of a force of less than 10 grams.

17. The method of claim 16, wherein at least two of the strands have different cross-sectional dimensions.

18. The method of claim 16, wherein at least two of the strands are of different metallic materials.

19. The method of claim 16, wherein at least some of the strands comprise platinum.

20. The method of claim 16, wherein the strands are round in cross section.

\* \* \* \* \*